United States Patent
Duan et al.

(10) Patent No.: US 11,778,908 B2
(45) Date of Patent: Oct. 3, 2023

(54) ORGANIC ELECTROLUMINESCENT DEVICES

(71) Applicants: Kunshan Go-Visionox Opto-Electronics Co., Ltd., Kunshan (CN); TSINGHUA UNIVERSITY, Beijing (CN)

(72) Inventors: Lian Duan, Kunshan (CN); Xiaozeng Song, Kunshan (CN); Dongdong Zhang, Kunshan (CN); Jinbei Wei, Kunshan (CN)

(73) Assignees: KUNSHAN GO-VISIONOX OPTO-ELECTRONICS CO., LTD., Kunshan (CN); TSINGHUA UNIVERSITY, Beijing (CN)

( * ) Notice: Subject to any disclaimer, the term of this patent is extended or adjusted under 35 U.S.C. 154(b) by 919 days.

(21) Appl. No.: 16/683,276

(22) Filed: Nov. 14, 2019

(65) Prior Publication Data

US 2020/0083461 A1    Mar. 12, 2020

Related U.S. Application Data

(63) Continuation of application No. PCT/CN2018/089397, filed on May 31, 2018.

(30) Foreign Application Priority Data

Dec. 29, 2017   (CN) .......................... 201711498154.8

(51) Int. Cl.
*H01L 51/00* (2006.01)
*C07D 209/86* (2006.01)
(Continued)

(52) U.S. Cl.
CPC ......... *H10K 85/6572* (2023.02); *C07C 13/72* (2013.01); *C07C 15/38* (2013.01);
(Continued)

(58) Field of Classification Search
None
See application file for complete search history.

(56) References Cited

U.S. PATENT DOCUMENTS

| | | | | |
|---|---|---|---|---|
| 5,759,444 A | * | 6/1998 | Enokida | ................. C09K 11/06 252/301.16 |
| 10,290,824 B2 | | 5/2019 | Nakanotani et al. | |

(Continued)

FOREIGN PATENT DOCUMENTS

| | | |
|---|---|---|
| CN | 103985822 A | 8/2014 |
| CN | 104716268 A | 6/2015 |

(Continued)

OTHER PUBLICATIONS

CN First Office Action with search report dated Jan. 19, 2020 in the corresponding CN application (application No. 201711498154.8).

(Continued)

*Primary Examiner* — Jay Yang
(74) *Attorney, Agent, or Firm* — KILPATRICK TOWNSEND & STOCKTON

(57) ABSTRACT

The present disclosure relates to display technologies, and particularly discloses an organic electroluminescent device. This organic electroluminescent device includes a light-emitting layer, the light-emitting includes an exciplex composed of a donor molecule and an acceptor molecule, and a wide band gap material for increasing the inter-molecular spacing between the donor molecule and the acceptor molecule. According to the device of the present disclosure, the degree of orbital overlap of HOMO and LUMO of the formed exciplex and the singlet-triplet energy level difference can be reduced, the reverse intersystem crossing rate ($k_{RISC}$) of the exciplex host can be increased, the Föster (Continued)

energy transferred to the guest molecule can be enhanced, and the efficiency and the lifetime of the device can be improved.

20 Claims, 5 Drawing Sheets

(51) Int. Cl.
| | |
|---|---|
| *C09K 11/06* | (2006.01) |
| *C07D 403/10* | (2006.01) |
| *C07C 211/54* | (2006.01) |
| *C07C 13/72* | (2006.01) |
| *C07F 9/6521* | (2006.01) |
| *C07C 15/38* | (2006.01) |
| *C07F 9/53* | (2006.01) |
| *C07D 401/14* | (2006.01) |
| *C07D 471/04* | (2006.01) |
| *H10K 85/60* | (2023.01) |
| *H10K 50/11* | (2023.01) |
| *H10K 101/10* | (2023.01) |

(52) U.S. Cl.
CPC .......... *C07C 211/54* (2013.01); *C07D 209/86* (2013.01); *C07D 401/14* (2013.01); *C07D 403/10* (2013.01); *C07D 471/04* (2013.01); *C07F 9/5329* (2013.01); *C07F 9/6521* (2013.01); *C09K 11/06* (2013.01); *H10K 85/633* (2023.02); *H10K 85/636* (2023.02); *H10K 85/654* (2023.02); *C07C 2603/44* (2017.05); *C07C 2603/97* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 85/626* (2023.02); *H10K 2101/10* (2023.02)

(56) References Cited

U.S. PATENT DOCUMENTS

| | | | |
|---|---|---|---|
| 10,312,453 | B2 | 6/2019 | Qiu et al. |
| 2006/0068223 | A1* | 3/2006 | Nariyuki ............... H05B 33/14 |
| | | | 428/917 |
| 2007/0141391 | A1* | 6/2007 | Coggan ............... H01L 51/0072 |
| | | | 428/917 |
| 2015/0214489 | A1* | 7/2015 | Parham ............... C07D 403/10 |
| | | | 252/301.16 |
| 2016/0315275 | A1 | 10/2016 | Seo et al. |
| 2017/0084844 | A1 | 3/2017 | Parham et al. |
| 2017/0194585 | A1 | 7/2017 | Yan |
| 2018/0248123 | A1 | 8/2018 | Ishisone et al. |

FOREIGN PATENT DOCUMENTS

| | | | |
|---|---|---|---|
| CN | 105895811 | A | 8/2016 |
| CN | 105957971 | A | 9/2016 |
| CN | 106103648 | A | 11/2016 |
| CN | 106450020 | A | 2/2017 |
| TW | 201600583 | A | 1/2016 |
| TW | 201628228 | A | 8/2016 |
| TW | 201735392 | A | 10/2017 |
| WO | WO-2014/015931 | A1 * | 1/2014 |
| WO | 2017006222 | A1 | 1/2017 |
| WO | 2017122492 | A1 | 7/2017 |
| WO | 2017169497 | A1 | 10/2017 |

OTHER PUBLICATIONS

TW First Office Action with search report dated May 10, 2019 in the corresponding TW application (application No. 107124202).
International Search Report dated Oct. 8, 2018 in the corresponding International application (application No. PCT/CN2018/089397).
He Liu, "The design synthesis and optoelectronic properties of organic wide-band-gap semiconductor based on tetraphenylsilane", May 23, 2014, 131 pages.(with English Abstract).

* cited by examiner

ORGANIC ELECTROLUMINESCENT DEVICES

CROSS-REFERENCES TO RELATED APPLICATIONS

This application is a continuation application for International Application PCT/CN2018/089397, filed on May 31, 2018, which claims the priority benefit of Chinese Patent Application No. 201711498154.8, titled "ORGANIC ELECTROLUMINESCENT DEVICES" and filed on Dec. 29, 2017. The entireties of both applications are incorporated by reference herein for all purposes.

TECHNICAL FIELD

The present disclosure relates to display technologies.

BACKGROUND

Organic electroluminescent devices, such as organic light-emitting diodes (OLEDs), have great application prospects in the field of display and illumination, and therefore attracted a lot of attention, due to their advantages such as ultra-thin, light weight, low power consumption, active illumination, wide viewing angle, fast response, and so on.

In 1987, C. W. Tang and Vanslyke of Eastman Kodak Company in the United States firstly reported two-layer organic electroluminescent devices based on Alq3 and tri-arylamines, and opened the direction of OLED research. Traditional fluorescent materials are easy to synthesize, cheap, stable, and have a long device lifetime. However, due to electron spin inhibition, only 25% of singlet excitons can be used for luminescence, and therefore the external quantum efficiency of the devices is often less than 5%, which need to be further improved.

SUMMARY

Therefore, the technical problem to be solved by the present disclosure is to overcome the existing problems, such as, energy level difference ($\Delta EST$) between the singlet and the triplet of the exciplex host material being relatively large, the rate of the reverse intersystem crossing being relatively low, the triplet-triplet annihilation (TTA) and triplet-polaron annihilation (TPA) in the light emitting layer being relatively serious, and the properties such as the device efficiency and the device lifetime needing to be further improved.

The present disclosure provides an organic electroluminescent device including a light-emitting layer, the light-emitting layer including a host material and a guest material, the host material including a wide band gap material and an exciplex composed of a donor molecule and an acceptor molecule.

Optionally, the triplet energy level of the wide band gap material is higher than the singlet energy level of the exciplex.

Optionally, triplet energy levels of the donor molecule and the acceptor molecule are respectively higher than the triplet energy level of the exciplex.

Optionally, the energy level difference between the singlet energy level and the triplet energy level of the exciplex is less than 0.15 eV.

Optionally, the wide band gap material is a compound containing at least one of a carbazolyl, an aryl, a diphenylphosphoryl, and a diphenyl ether.

Optionally, the wide band gap material is selected from at least one of the compounds of structures shown below:

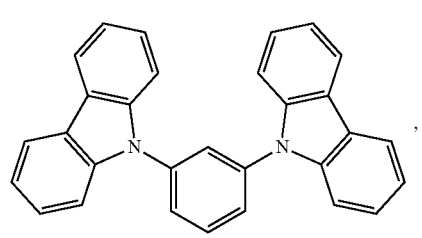

(W-1)

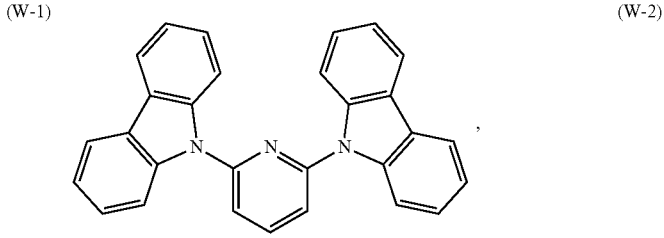

(W-2)

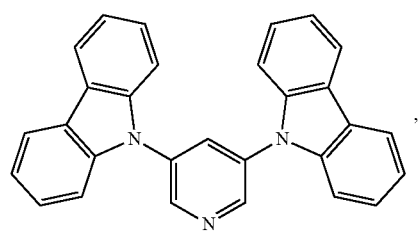

(W-3)

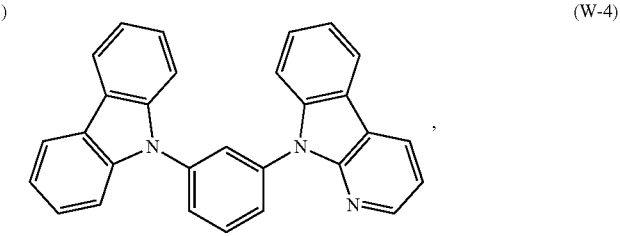

(W-4)

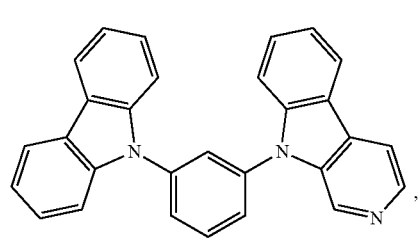

(W-5)

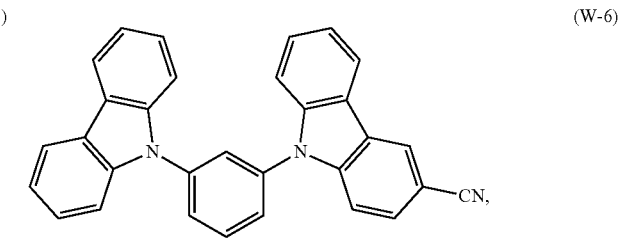

(W-6)

-continued
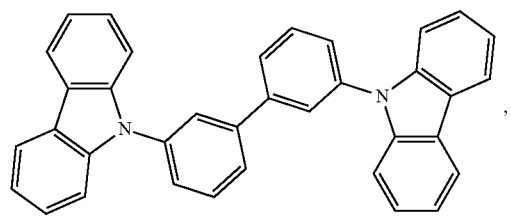 (W-7)
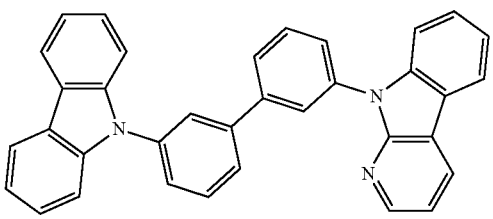 (W-8)
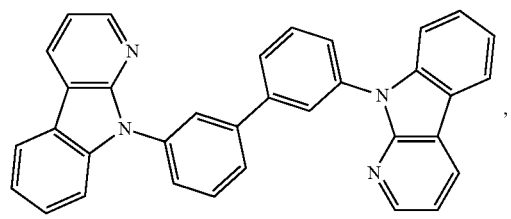 (W-9)
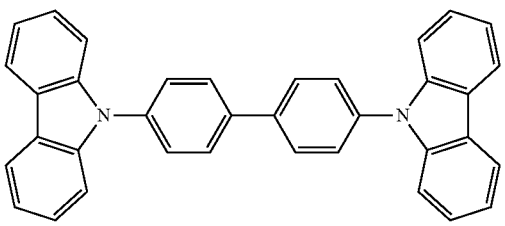 (W-10)
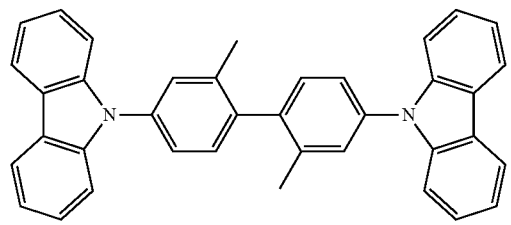 (W-11)
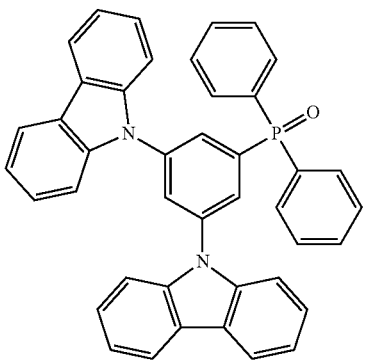 (W-12)
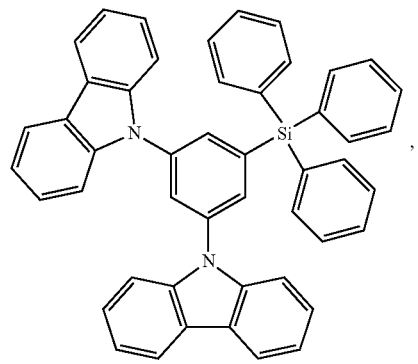 (W-13)
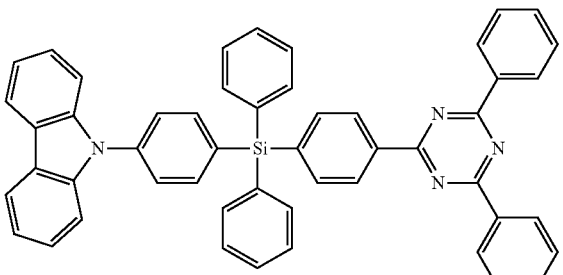 (W-14)

-continued
(W-15)
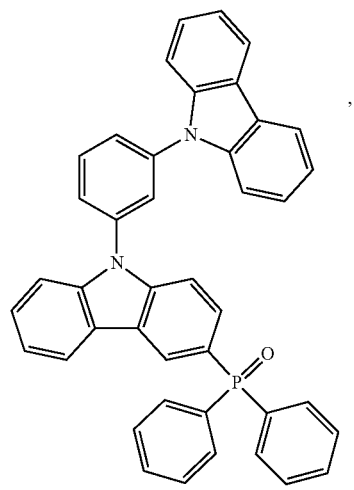
(W-16)
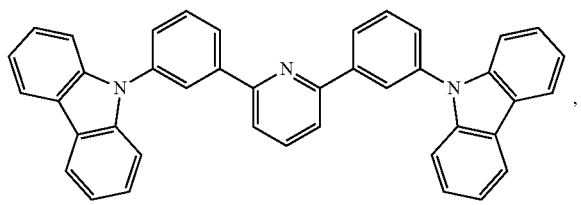
(W-17)
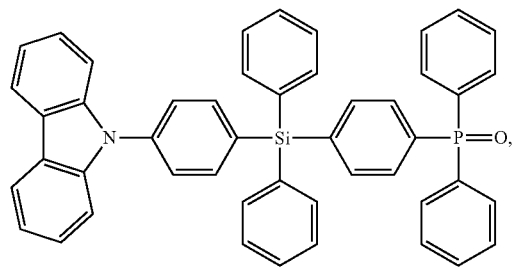
(W-18)
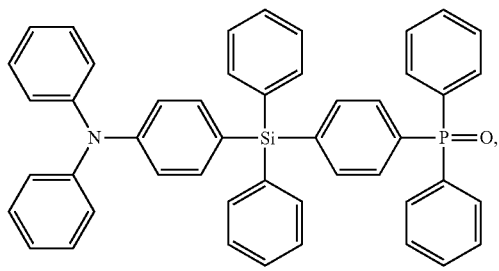
(W-19)
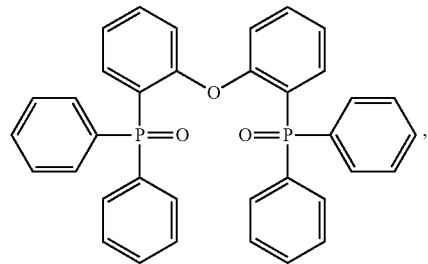
(W-20)
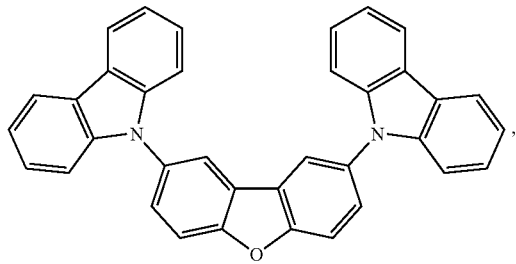
(W-21)
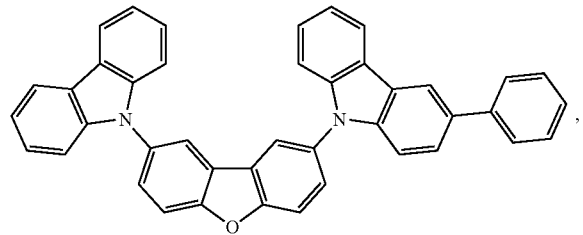
(W-22)
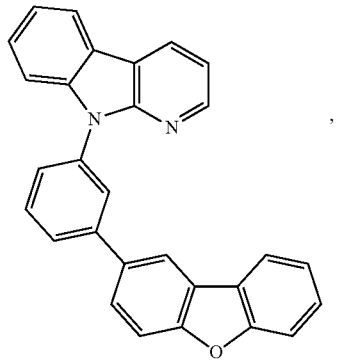

-continued
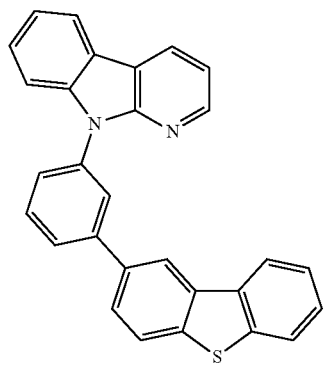
(W-23)
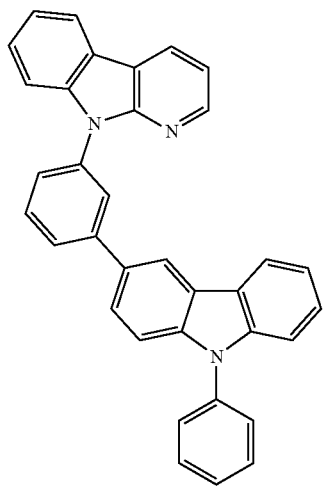
(W-24)
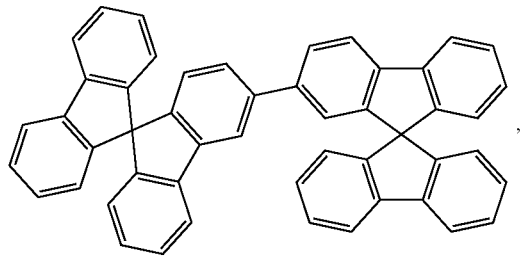
(W-25)
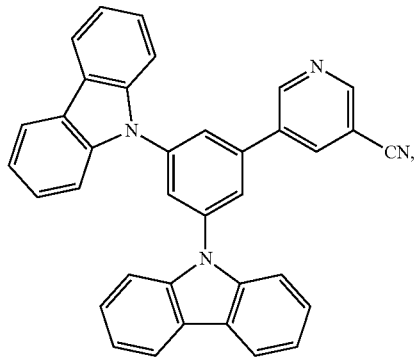
(W-26)
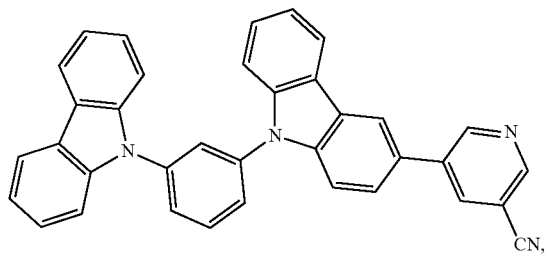
(W-27)
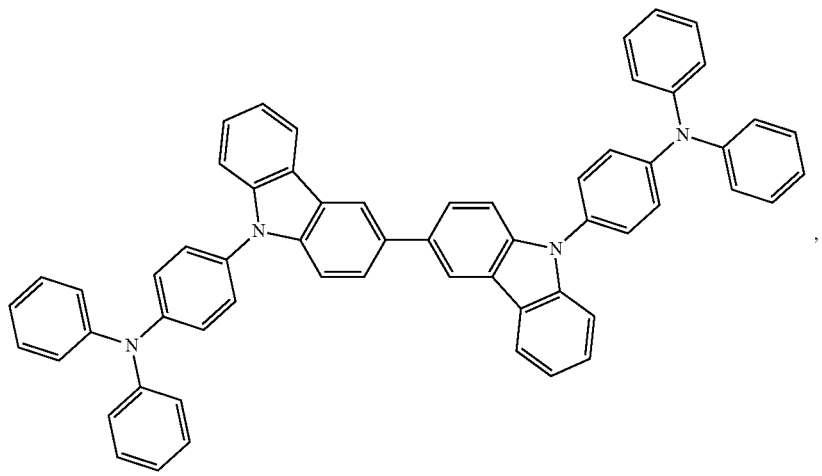
(W-28)

-continued
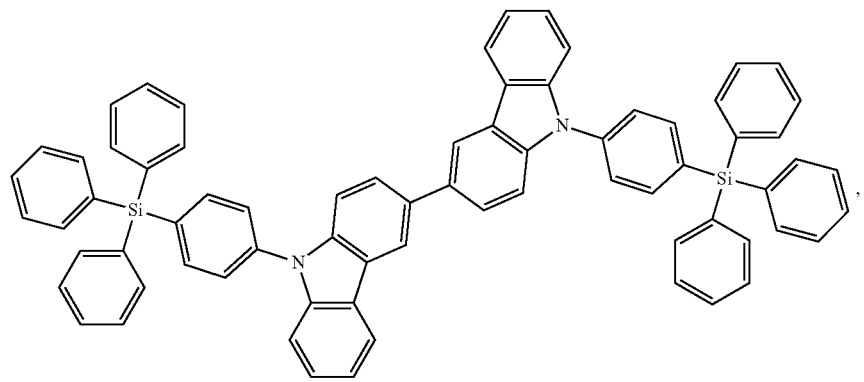
(W-29)
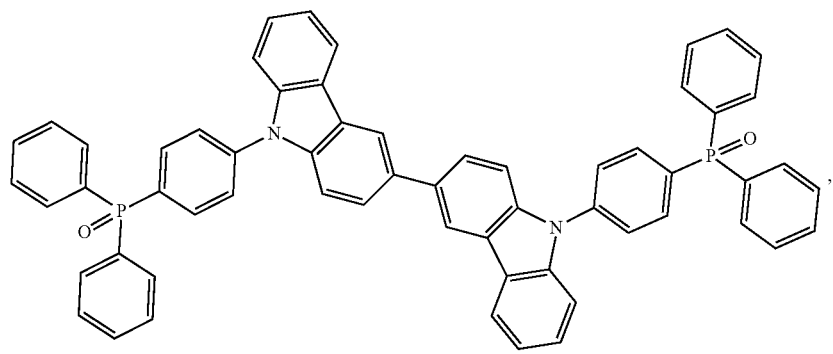
(W-30)
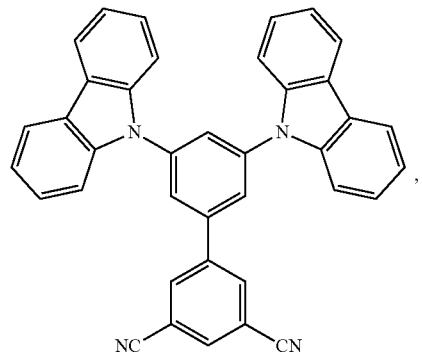
(W-31)
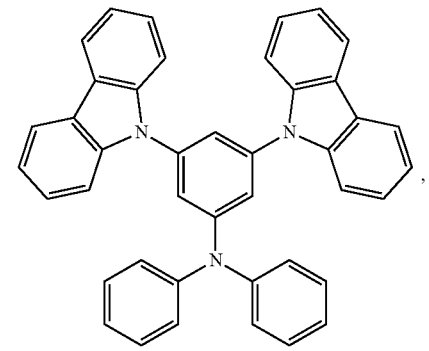
(W-32)
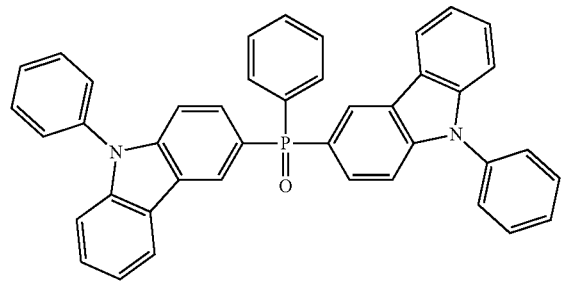
(W-33)
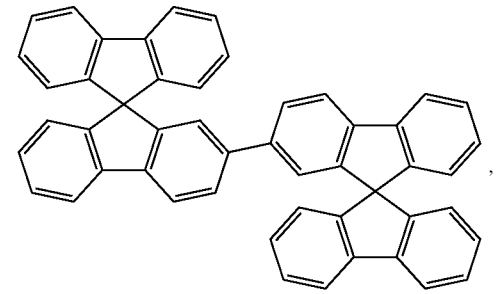
(W-34)

-continued
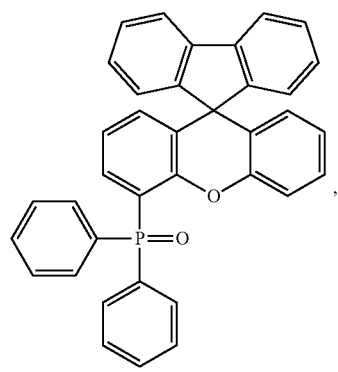
(W-35)
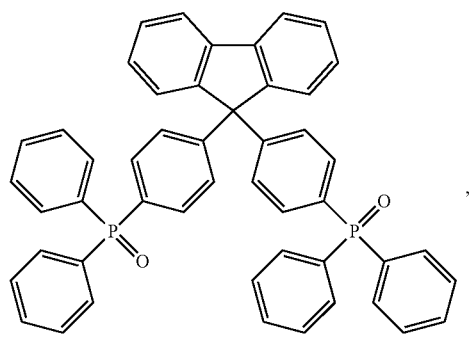
(W-36)
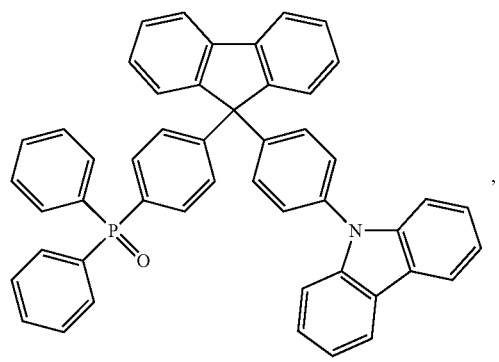
(W-37)
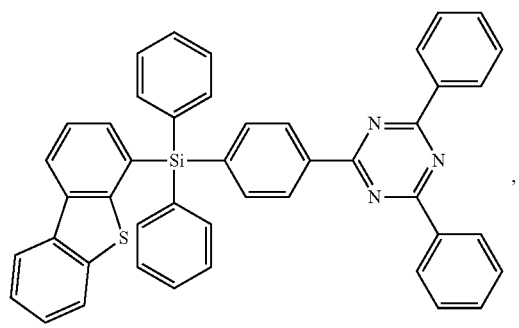
(W-38)
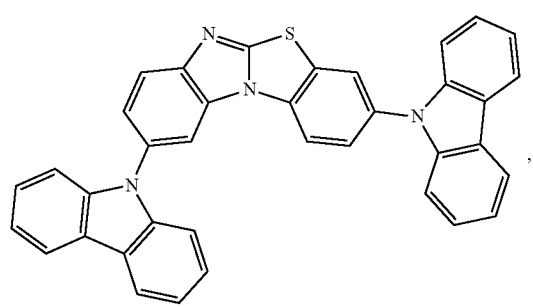
(W-39)
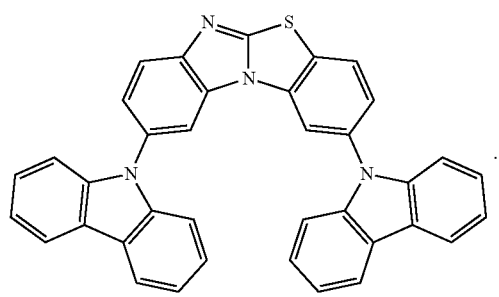
(W-40)

Optionally, the donor molecule is a compound having hole transport property and containing at least one of a carbazolyl, a triphenylamine, and an aryl.
Optionally, the donor molecule is selected from at least one of the compounds of structures shown below:
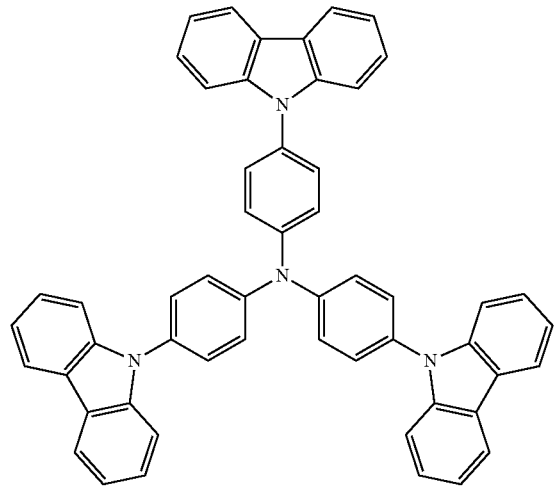
(D-1)
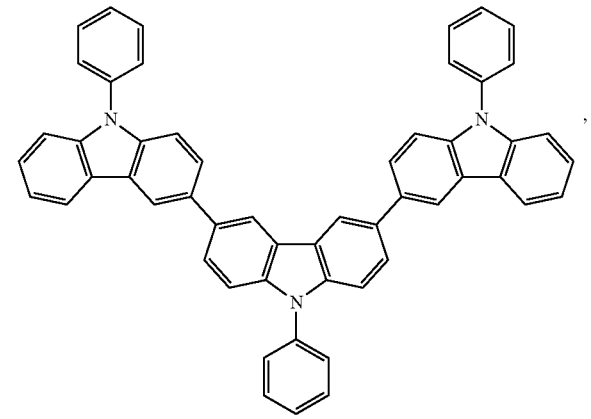
(D-2)
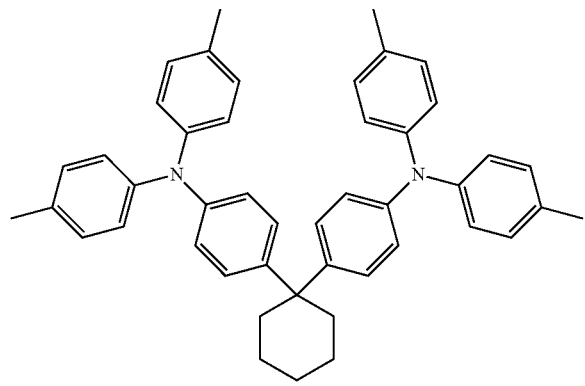
(D-3)
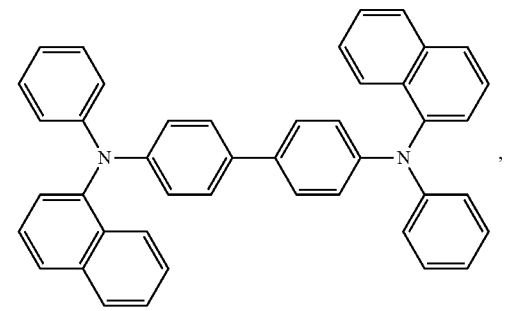
(D-4)
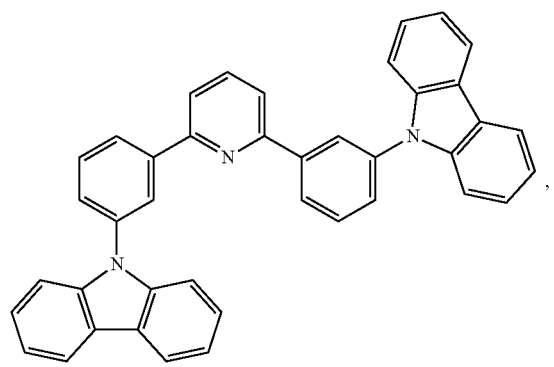
(D-5)
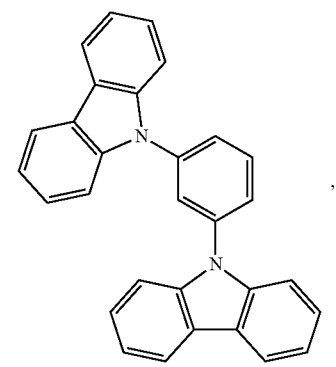
(D-6)

-continued
(D-7)
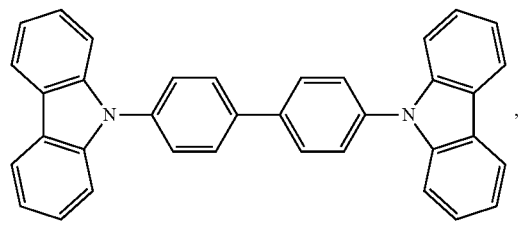
(D-8)
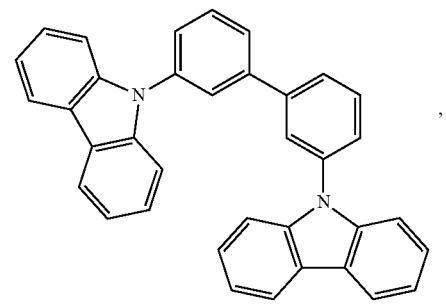
(D-9)
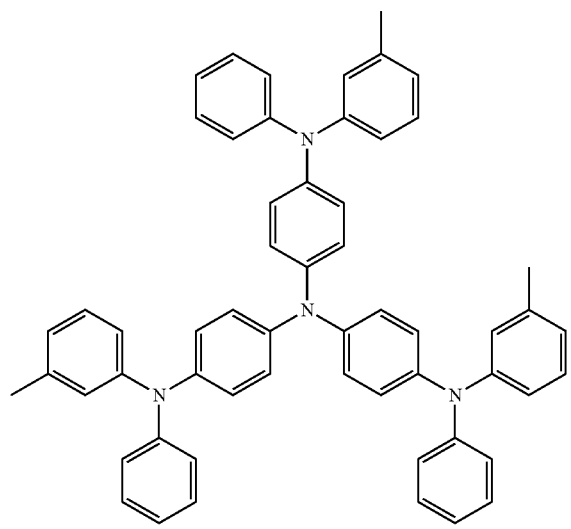
(D-10)
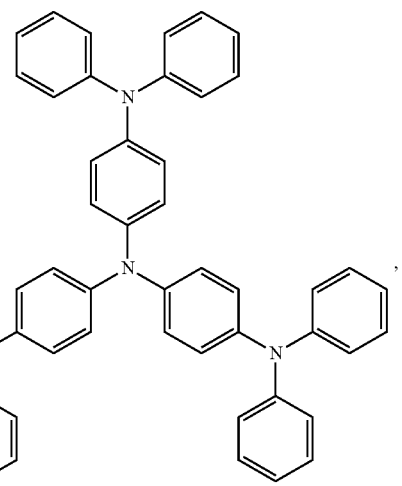
(D-11)
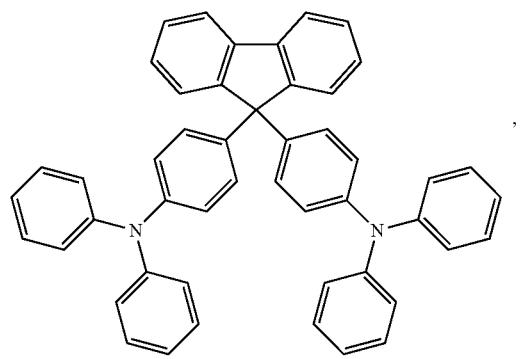
(D-12)
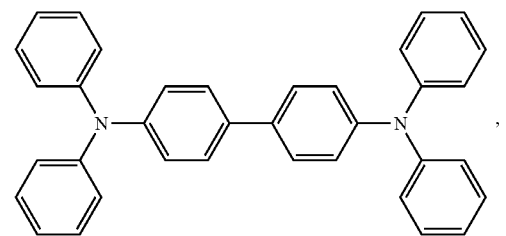
(D-13)
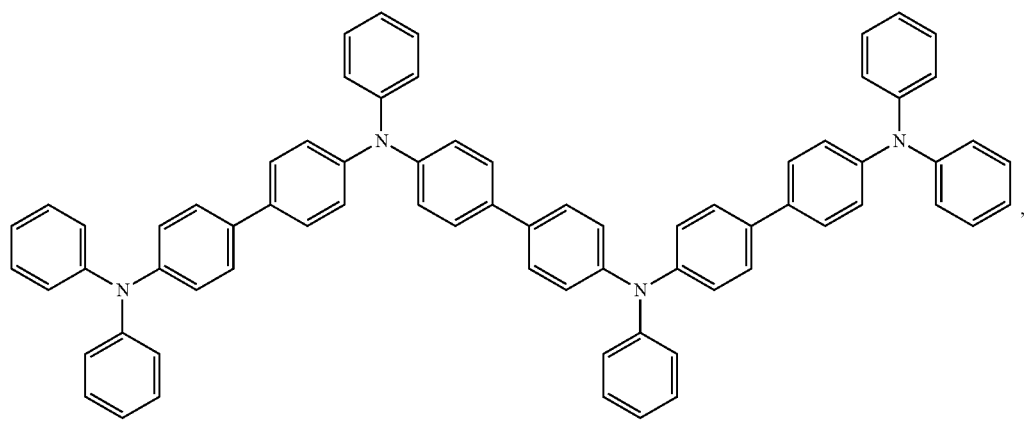

(D-14)
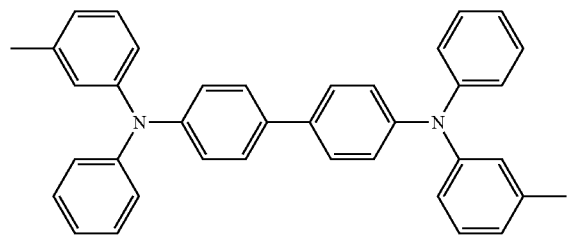
(D-15)
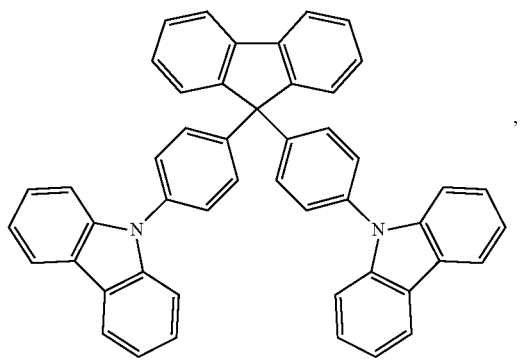
(D-16)
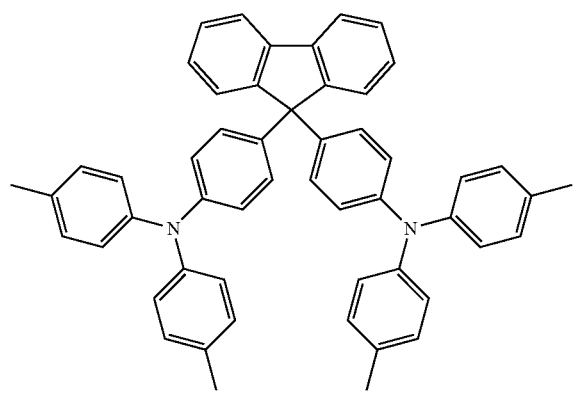
(D-17)
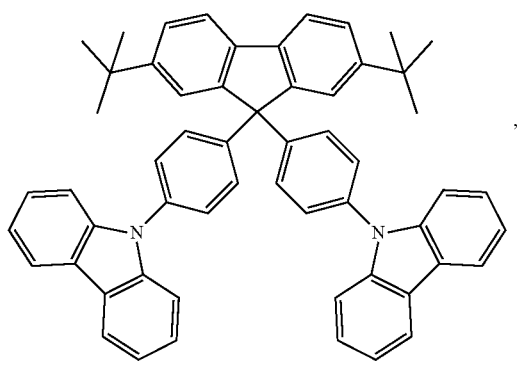
(D-18)
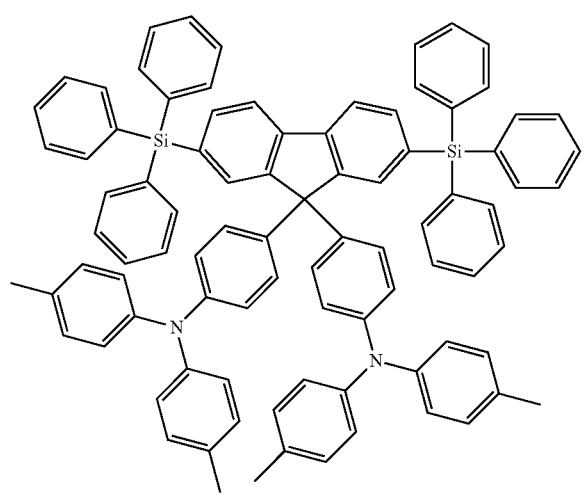

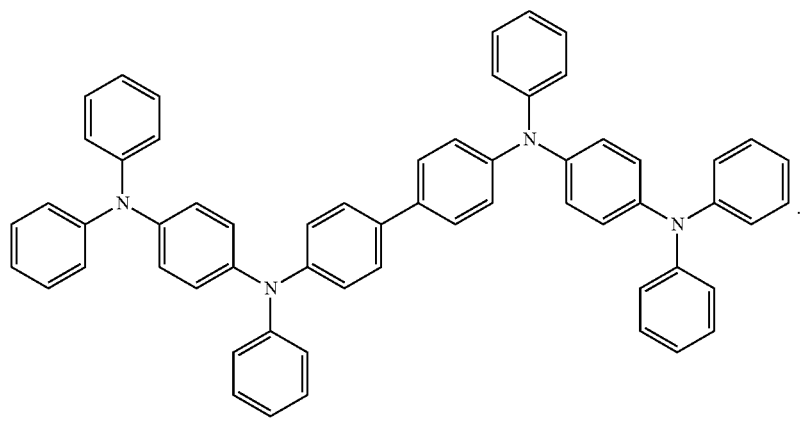
(D-19)
Optionally, the acceptor molecule is a compound having electron transport property and containing at least one of a pyridyl, a pyrimidinyl, a triazinyl, a carbazolyl, an aryl, a cyano, and a diphenylphosphono.
Optionally, the acceptor molecule is selected from at least one of the compounds of structures shown below:
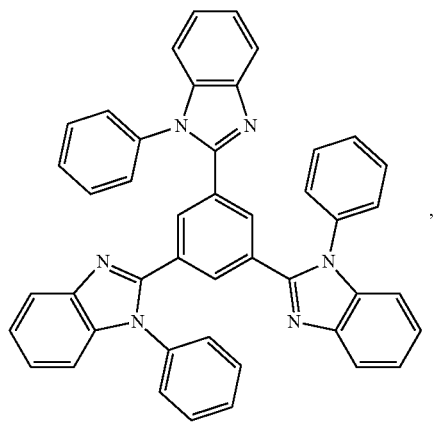
(A-1)
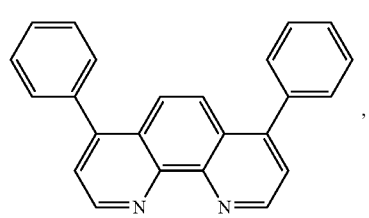
(A-2)
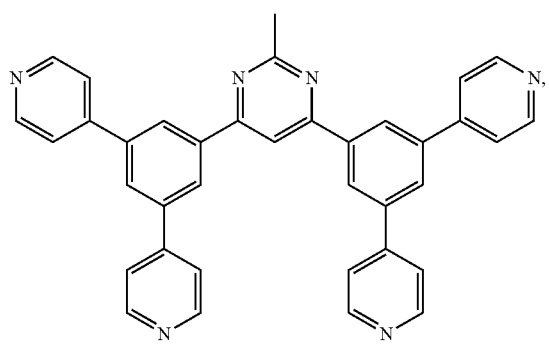
(A-3)
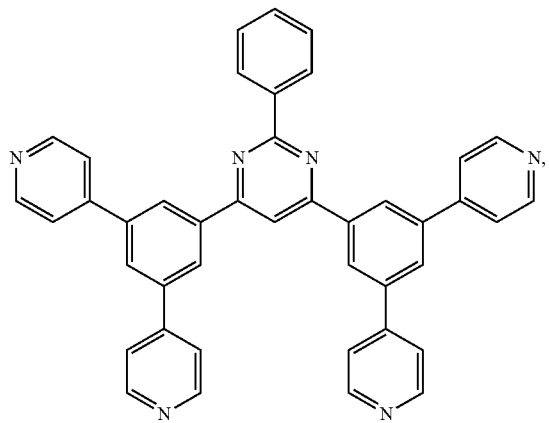
(A-4)

(A-5)
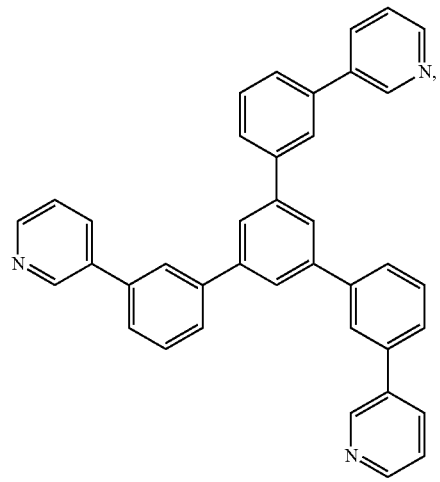
(A-6)
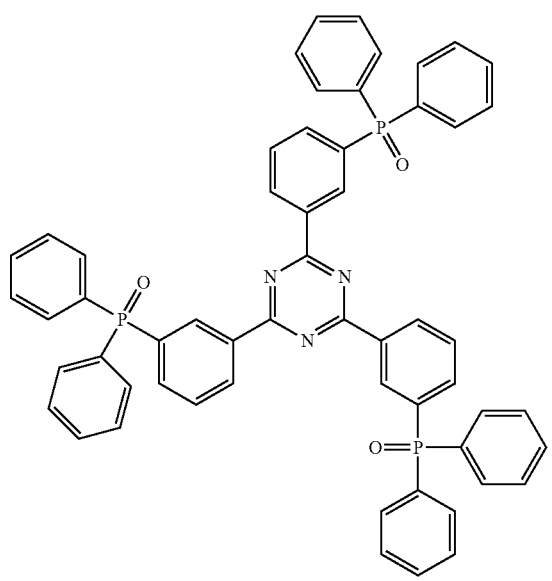
(A-7)
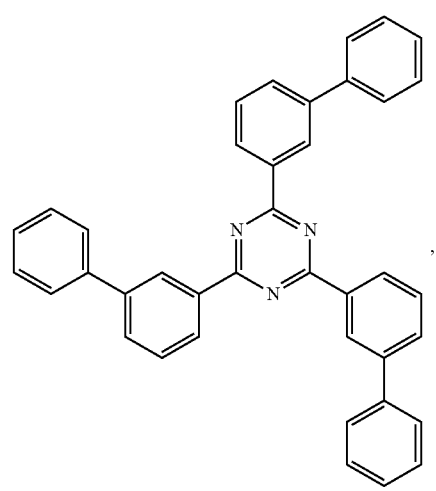
(A-8)
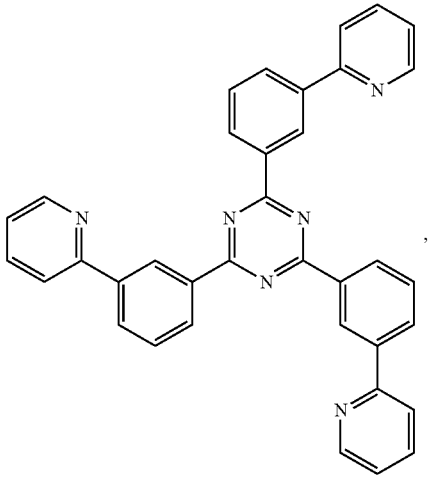
(A-9)
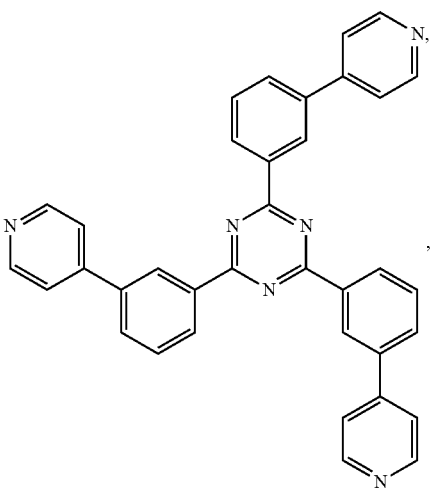
(A-10)
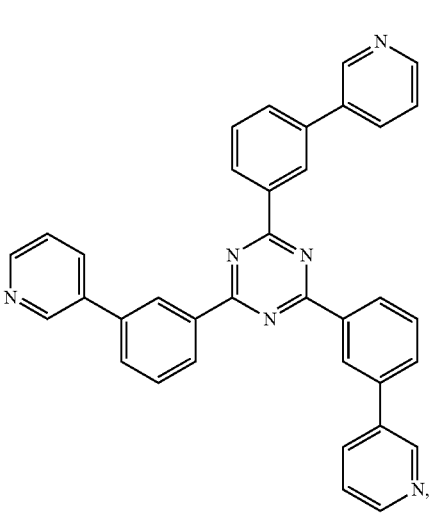

(A-11)
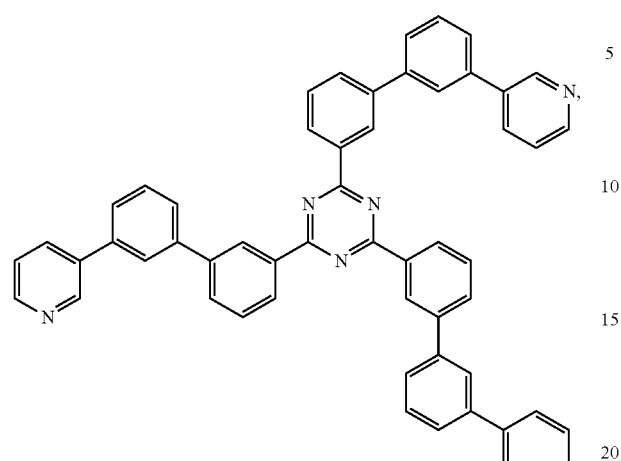
(A-12)
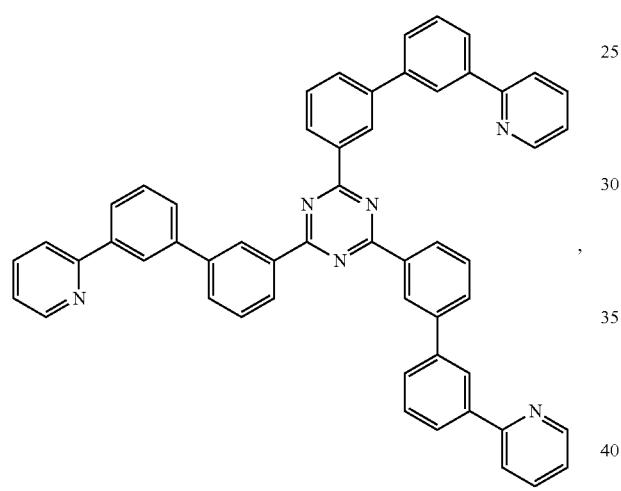
(A-13)
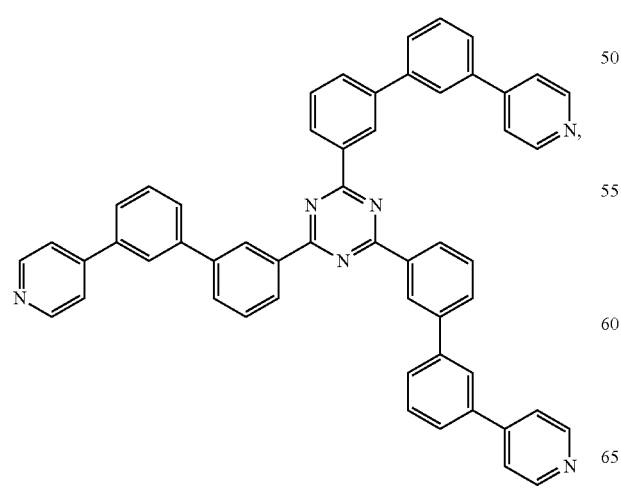
(A-14)
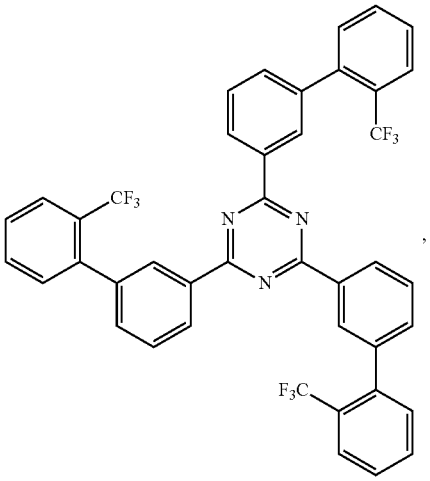
(A-15)
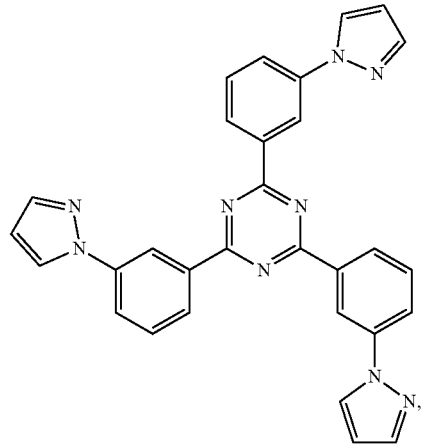
(A-16)
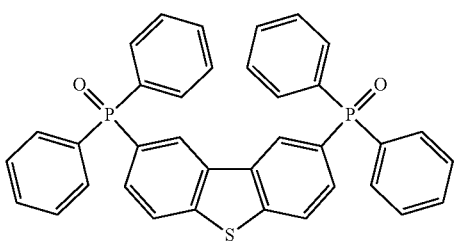
(A-17)
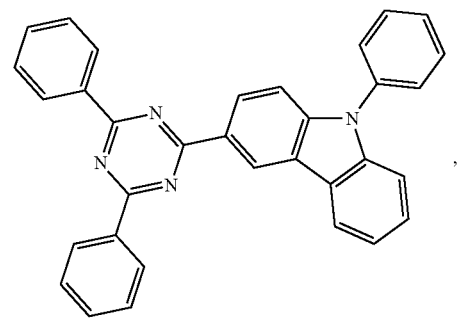

(A-18)
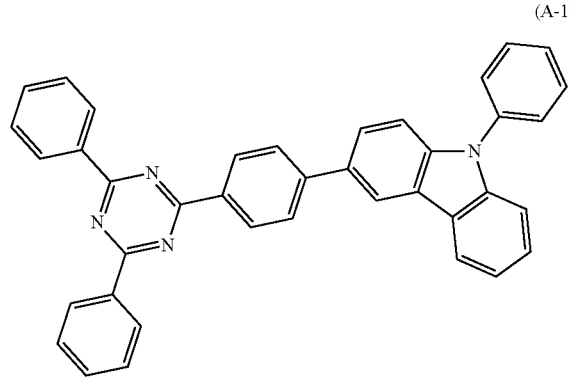
(A-19)
(A-20)
(A-21)
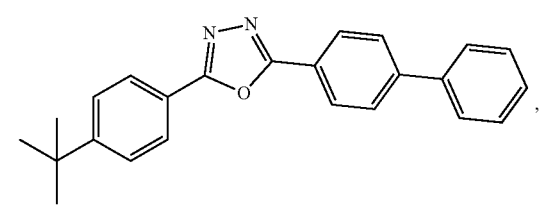
(A-22)
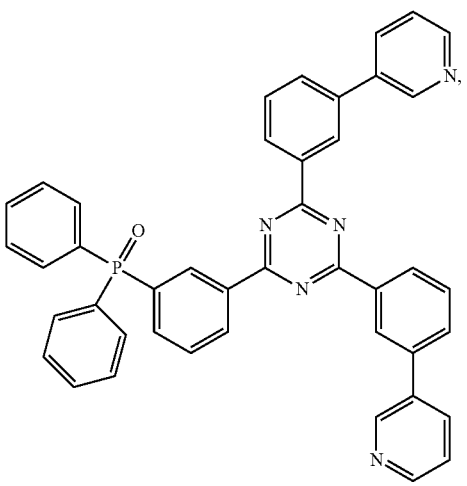
(A-23)
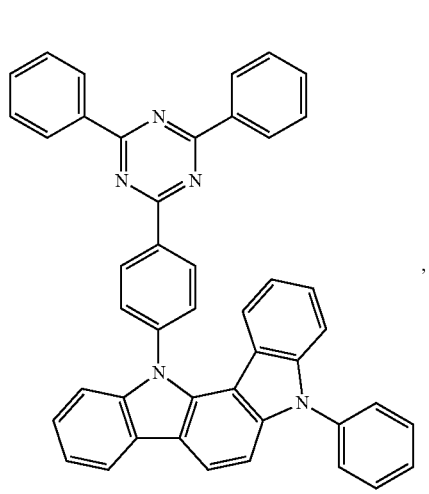
(A-24)
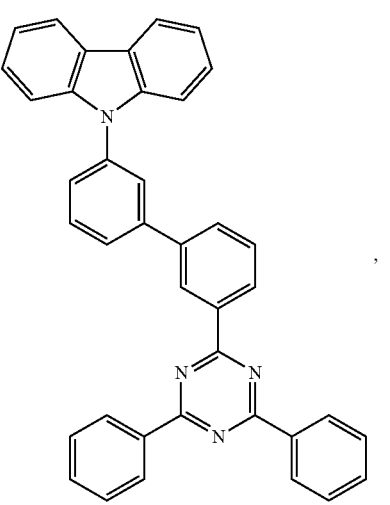

(A-25)
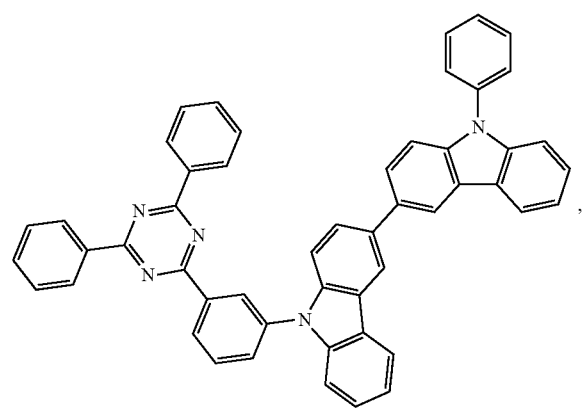
(A-26)
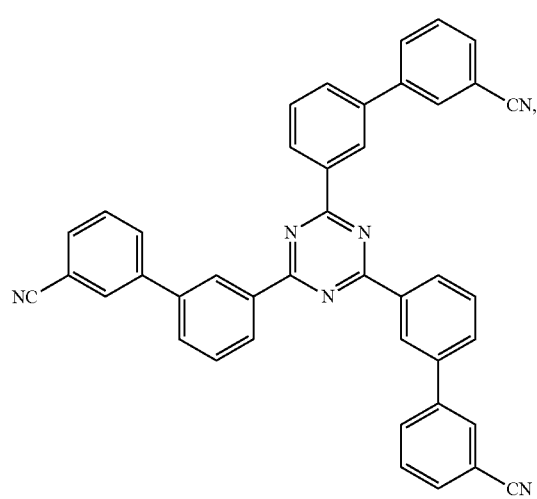
(A-27)
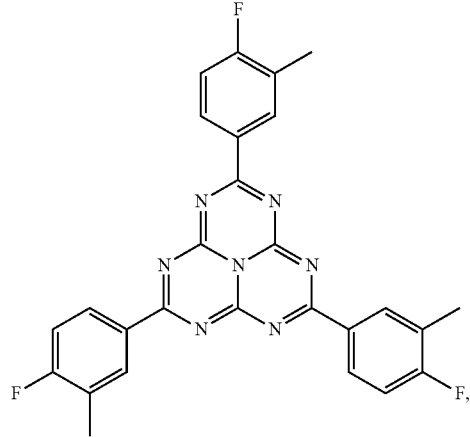
(A-28)
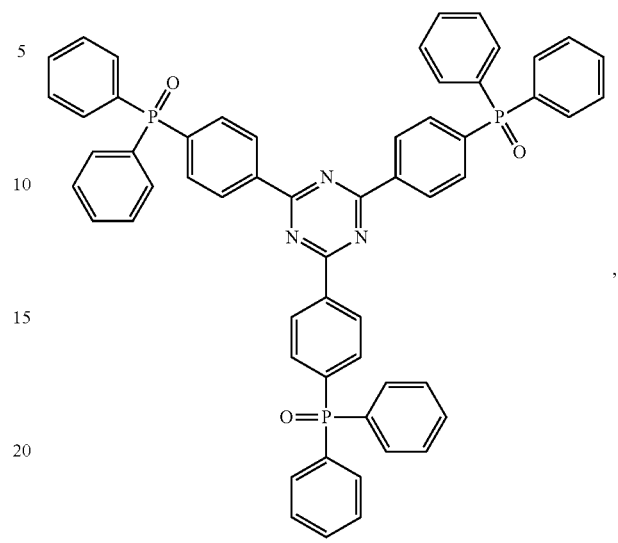
(A-29)
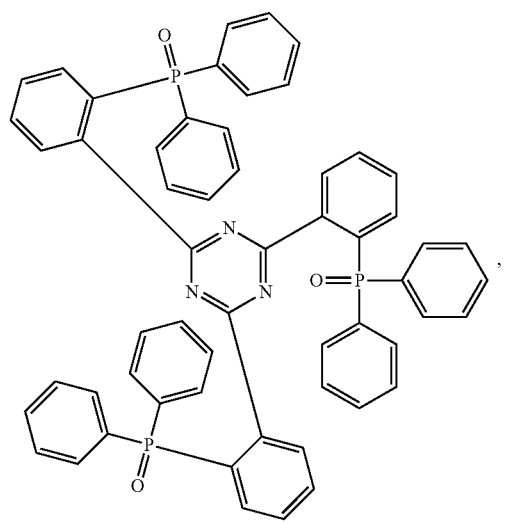
(A-30)
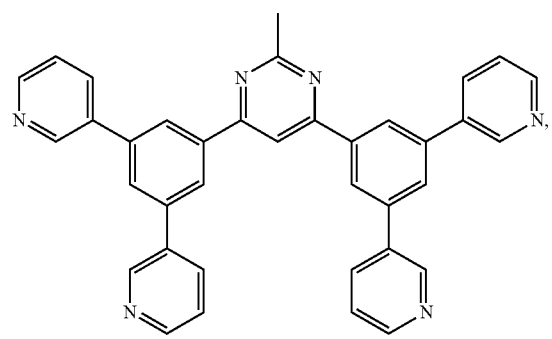

(A-31)
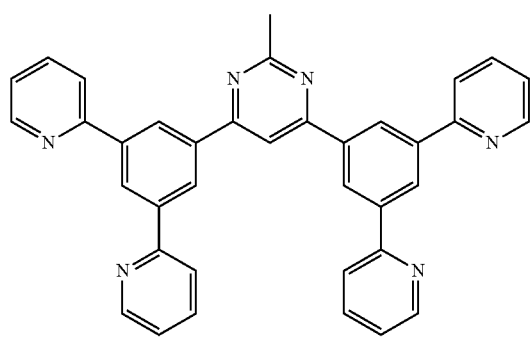
(A-32)
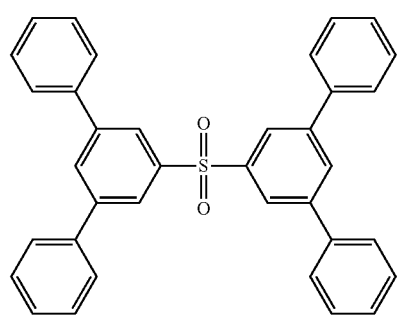
(A-33)
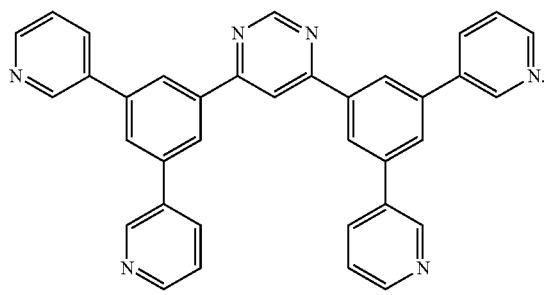
Optionally, in the exciplex, the mass ratio of the donor molecule to the acceptor molecule is between 1:9 and 9:1, preferably between 1:5 and 5:1.
Optionally, the guest material is a fluorescent doping dye, and the fluorescent doping dye is selected from at least one of the compounds of structures shown below:
(F-1)
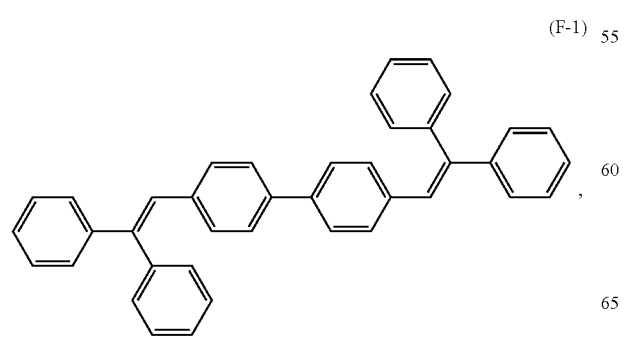
(F-2)
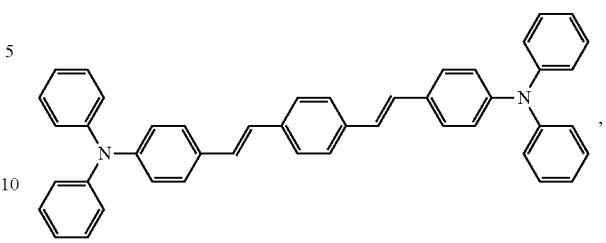
(F-3)
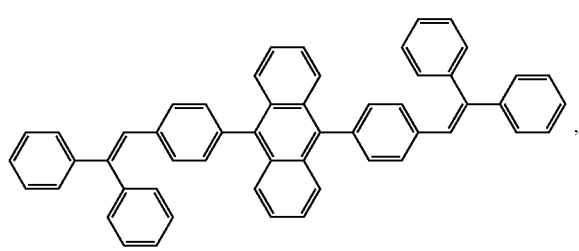
(F-4)
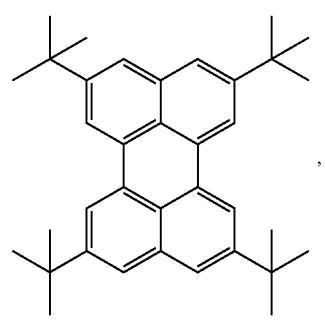
(F-5)
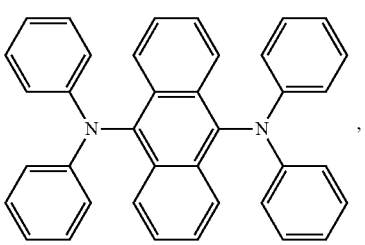
(F-6)
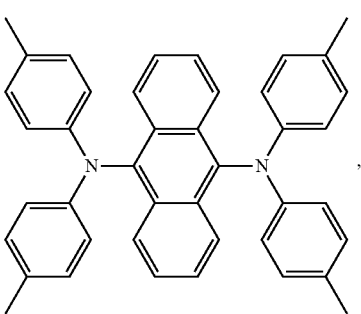

(F-7)
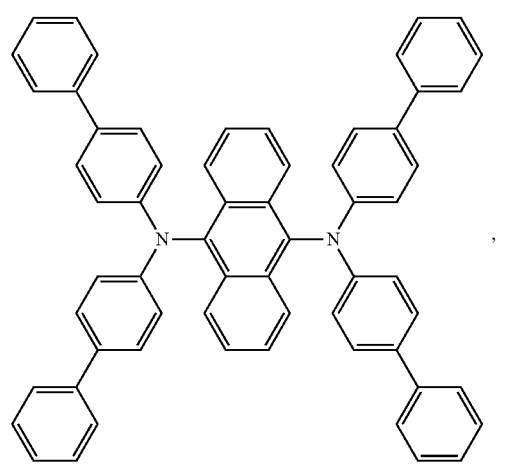
(F-8)
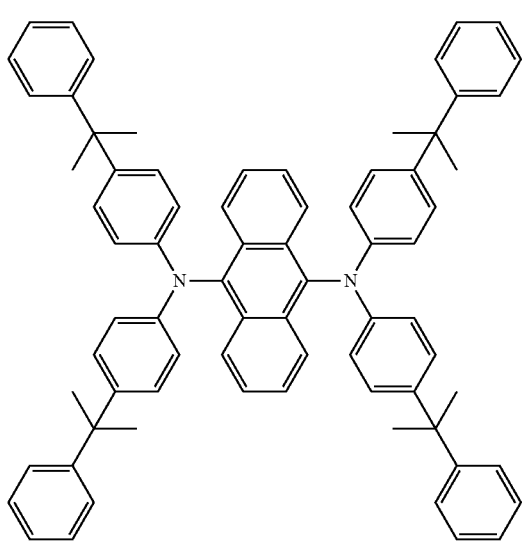
(F-9)
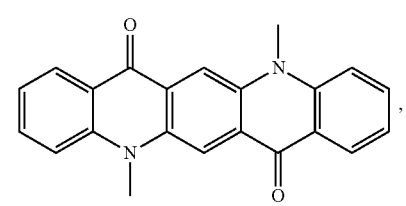
(F-10)
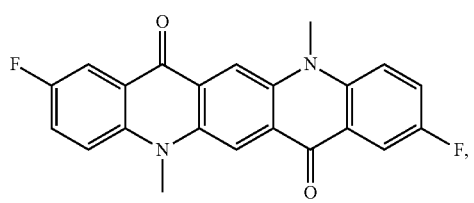
(F-11)
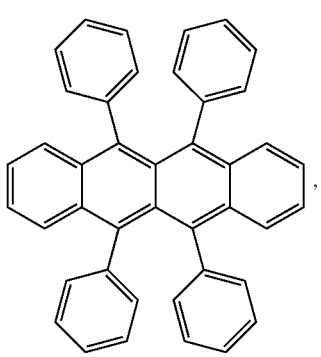
,
(F-12)
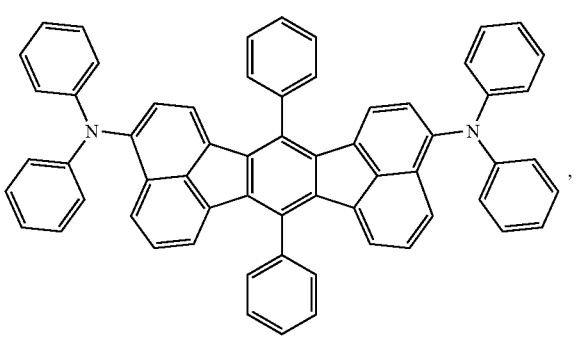
,
(F-13)
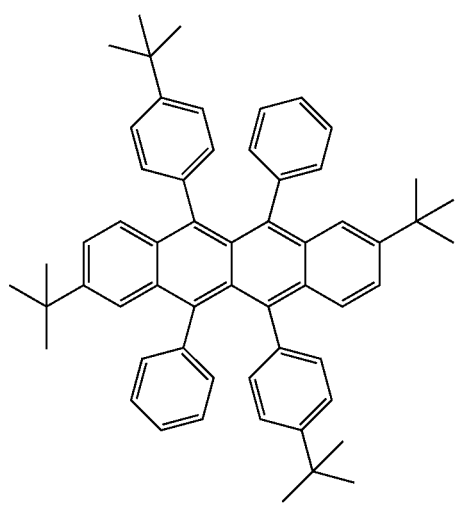
,
(F-14)
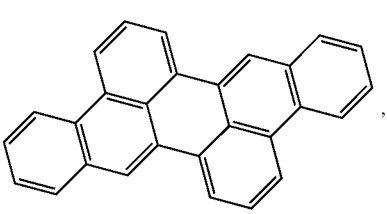
,

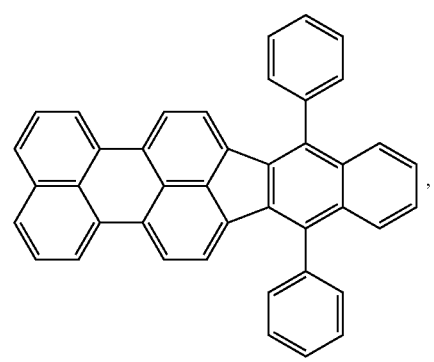
(F-15)
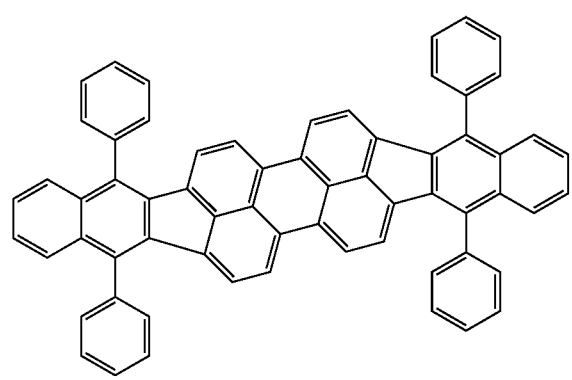
(F-16)
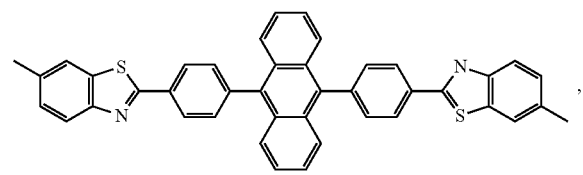
(F-17)
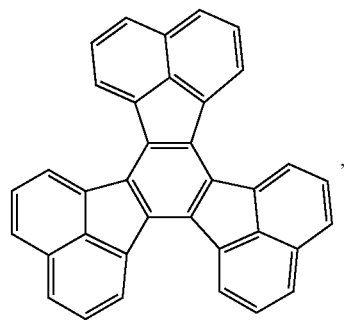
(F-18)
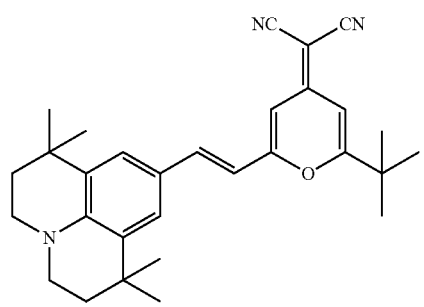
(F-19)
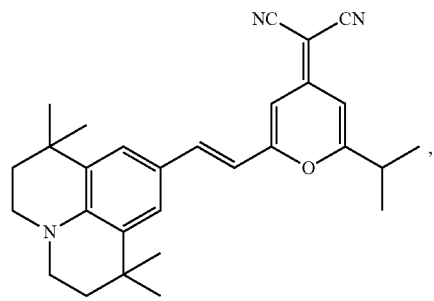
(F-20)
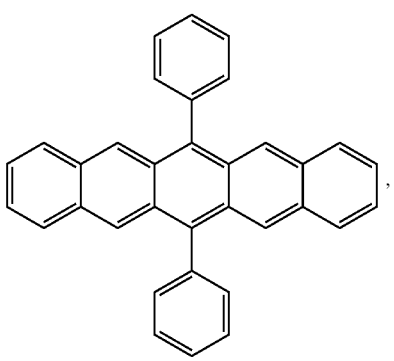
(F-21)
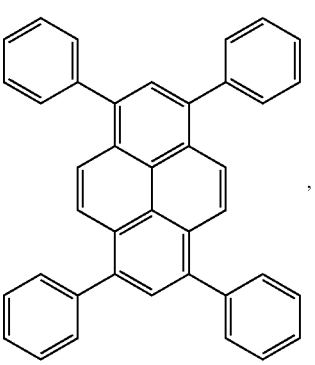
(F-22)
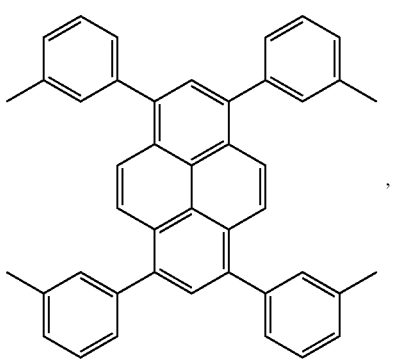
(F-23)

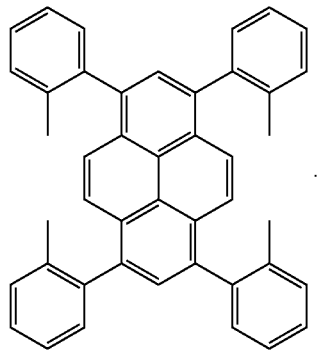
(F-24)

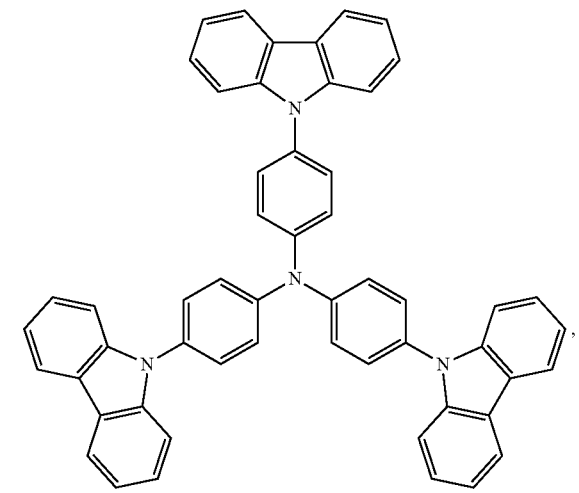
(D-1)

Optionally, the doping ratio of the exciplex is between 5 wt % and 80 wt % (the doping ratio of the exciplex refers to the ratio of the mass of the exciplex to the total mass of the light-emitting layer).

Optionally, the doping ratio of the fluorescent doping dye is between 0.1 wt % and 10 wt % (the doping ratio of the fluorescent doping dye refers to the ratio of the mass of the fluorescent doping dye to the total mass of the light-emitting layer).

Optionally, the content of the exciplex is between 20 wt % and 50 wt % based on the total weight of the light-emitting layer.

Optionally, the content of the fluorescent doping dye is between 0.1 wt % and 3 wt % based on the total weight of the light-emitting layer.

Optionally, the organic electroluminescent device includes a first electrode, a second electrode, and an organic functional layer between the first electrode and the second electrode, the organic functional layer including a hole injection layer, a hole transport layer, the light-emitting layer described above, an electron transport layer, and an electron injection layer 35 which are stacked.

Optionally, the wide band gap material is a compound as represented by a formula (W-1), the donor molecule is a compound as represented by a formula (D-1), and the acceptor molecule is a compound as represented by a formula (A-19):

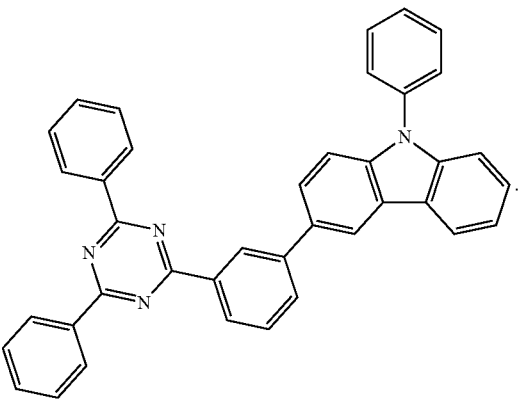
(A-19)

Optionally, the guest material is a fluorescent doping dye, the fluorescent doping dye being a compound as represented by a formula (F-8):

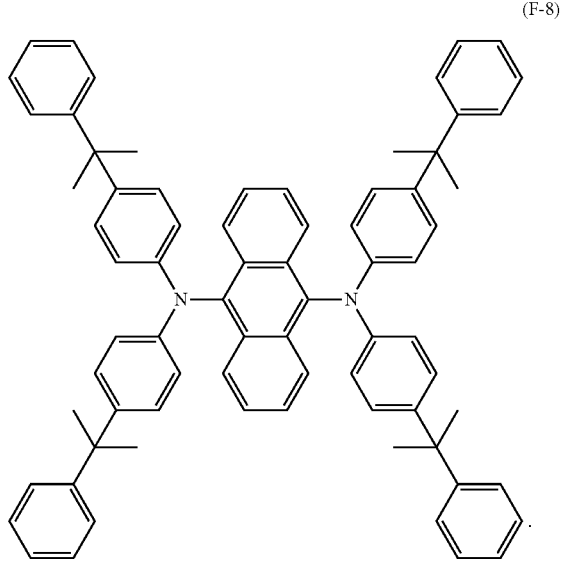 [SMILES: CC(C)(c1ccccc1)c1ccc(N(c2ccc(C(C)(C)c3ccccc3)cc2)c2c3ccccc3c(N(c3ccc(C(C)(C)c4ccccc4)cc3)c3ccc(C(C)(C)c4ccccc4)cc3)c3ccccc23)cc1]
(F-8)

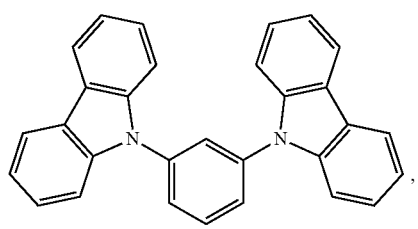
(W-1)

The technical solution of the present disclosure has the following advantages:

As described above, the organic electroluminescent device provided by the present disclosure has a first electrode, a second electrode, and an organic functional layer between the first electrode and the second electrode, the organic functional layer including a light-emitting layer, and the light-emitting layer including a host material and a guest material. The host material includes a wide band gap material and an exciplex composed of a donor molecule and an acceptor molecule.

Firstly, by introducing a wide band gap material, the distance between the donor molecule and the acceptor molecule is increased, the degree of overlap between the HOMO and LUMO of the formed exciplex body is reduced, and the singlet-triplet energy level difference $\Delta E_{ST}$ is reduced, thereby increasing the reverse intersystem crossing rate ($k_{RISC}$) of the exciplex, the excitons are easily returned from the triplet to the singlet by the reverse intersystem crossing process, which greatly improves the utilization rate of excitons; suppresses the Dexter energy transfer and improves the luminous efficiency of the device at the same time.

Secondly, the introduction of the wide bandgap material increases the distance between the donor molecule and the acceptor molecule in the exciplex, reduces the concentration of the triplet exciton in the light-emitting layer, and suppresses the triplet-triplet annihilation (TTA) and triplet-polaron annihilation (TPA), which helps to reduce the efficiency roll-off of the device and improve the lifetime of the electroluminescent device.

BRIEF DESCRIPTION OF THE DRAWINGS

To describe the technical solutions of the embodiments of the present disclosure or the prior art more clearly, the following briefly introduces the accompanying drawings required for describing the embodiments or the prior art. Apparently, the accompanying drawings in the following description show some embodiments of the present disclosure, and persons skilled in the art may also derive other drawings from these accompanying drawings without creative efforts.

DETAILED DESCRIPTION OF THE INVENTION

In order to reduce the cost and break through the limitation of 25% internal quantum efficiency in OLED devices, a mechanism of Thermally Activated Delayed Fluorescence (TADF) was proposed. In small organic molecular materials having small singlet-triplet energy level difference ($\Delta EST$), the triplet excitons can be converted to singlet excitons through the reverse intersystem crossing (RISC) process by absorbing ambient heat, theoretically the internal quantum efficiency of the device can reach 100%. However, the reported TADF material has a relatively large efficiency roll-off and short lifetime, which limits its application in full-color display and white light illumination.

The technical solutions of the present disclosure are clearly and completely described in the following with reference to the accompanying drawings. It is obvious that the described embodiments are a part of the embodiments of the present disclosure, and not all of the embodiments. All other embodiments obtained by persons skilled in the art based on the embodiments of the present disclosure without creative efforts shall fall within the protection scope of the present disclosure.

In the description of the present disclosure, it is to be noted that the terms "first", "second", and "third" are used for descriptive purposes only, and are not to be construed as indicating or implying relative importance.

The present disclosure may be implemented in many different forms and should not be construed as being limited to the embodiments set forth herein. In contrast, these embodiments are provided so that the present disclosure will be thorough and complete, and the concept of the present disclosure will be fully conveyed to those skilled in the art, and the present disclosure will only be defined by the claims. In the accompanying drawings, dimensions and relative dimensions of layers and regions may be exaggerated for clarity. It should be understood that when an element such as a layer is referred to as "formed" or "provided on" another element, the element may be provided directly on another element, or there may be an intermediate element. In contrast, when an element is refer to as "directly formed on" or "directly provided on" another element, there is no intermediate element.

Embodiment 1

Figure 1:
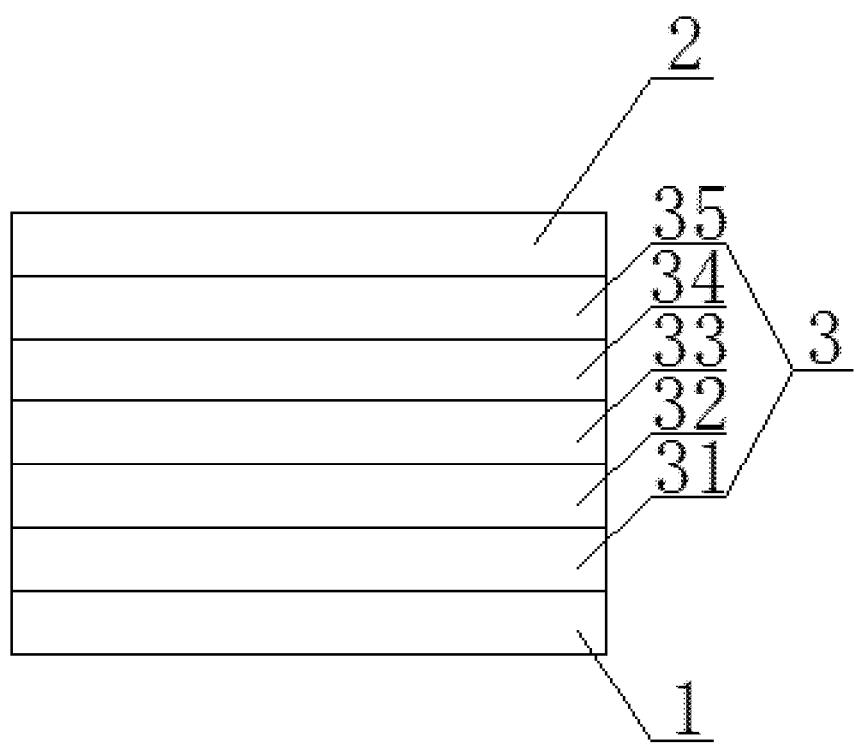
FIG. 1 is a schematic structural view of an organic electroluminescent device according to Embodiment 1 of the present disclosure.

The present embodiment provides an organic electroluminescent device having a first electrode 1, a second electrode 2, and an organic functional layer 3 between the first electrode 1 and the second electrode 2, as shown in FIG. 1. The first electrode 1 is an anode, the second electrode 2 is a cathode, and the organic functional layer 3 includes a hole injection layer 31, a hole transport layer 32, a light-emitting layer 33, an electron transport layer 34, and an electron injection layer 35 which are stacked, that is, the structure of this organic electroluminescent device is: anode/hole injection layer/hole transport layer/light-emitting layer/electron transport layer/electron injection layer/cathode.

The light-emitting layer 33 is composed of a host material and a doping material doped in the host material. The wide band gap material and the exciplex form the host material by a co-evaporation method, the donor molecule and the acceptor molecule form the exciplex by a co-evaporation method, and the wide band gap material dilutes the exciplex to increase the distance between the donor molecule and the acceptor molecule. The doping material is a fluorescent doping dye.

In the light-emitting layer 33, the doping ratio of the exciplex is between 5 wt % and 80 wt %, the doping ratio of the fluorescent doping dye is between 0.1 wt % and 10 wt %, and the rest are wide band gap materials; preferably, the content of the exciplex is between 20 wt % and 50 wt %, and the content of the fluorescent doping dye is between 0.1 wt % and 3 wt %. Wherein the exciplex is composed of a donor molecule and an acceptor molecule, and the donor molecule is a compound having hole transport property and containing at least one of a carbazolyl, a triphenylamine and an aryl, the acceptor molecule is a compound having electron transport property and containing at least one of a pyridyl group, a pyrimidinyl group, a triazinyl group, a carbazolyl group, an aryl group, a cyano group, and a diphenylphosphono group. In the exciplex, the mass ratio of the donor molecule to the acceptor molecule is between 1:9 and 9:1, preferably 1:5 and 5:1.

In this embodiment, a compound containing a carbazolyl and a phenyl, as represented by the formula (W-1), is selected as the wide band gap material:

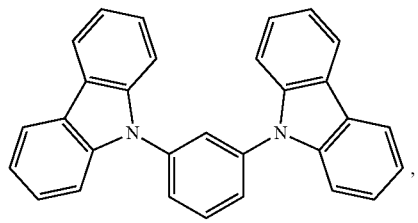
(W-1)

a compound containing a phenyl and a carbazolyl, as represented by the formula (D-1), is selected as the donor molecule:

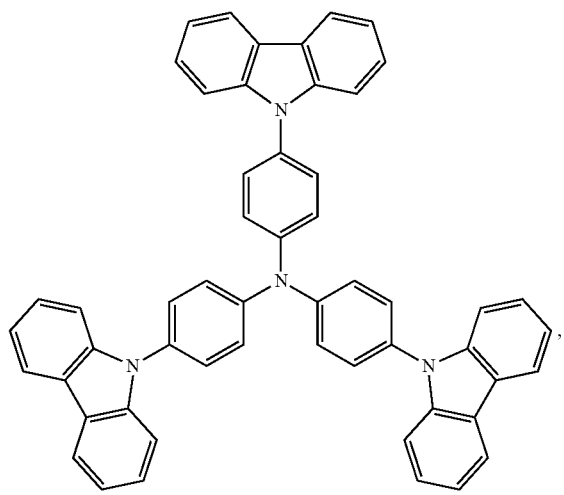
(D-1)

a compound containing a phenyl, a triazinyl and a carbazolyl, as represented by the formula (A-19), is selected as the acceptor molecule:

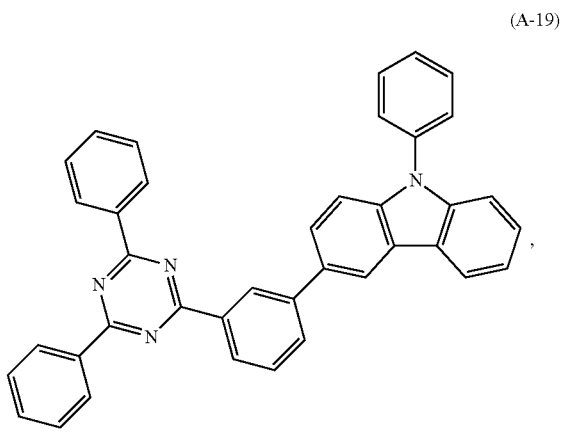 [SMILES: c1ccc(-c2nc(-c3ccccc3)nc(-c3cccc(-c4ccc5c(c4)c4ccccc4n5-c4ccccc4)c3)n2)cc1]
(A-19)

the donor molecule shown by formula (D-1) and the acceptor molecule shown by the formula (A-19) constitute an exciplex, and in the exciplex, the mass ratio of the donor molecule shown by the formula (D-1) to the acceptor molecule shown by formula (A-19) is 1:1.

A fluorescent doping dye having a structure shown by the formula (F-8) is selected as the doping material:

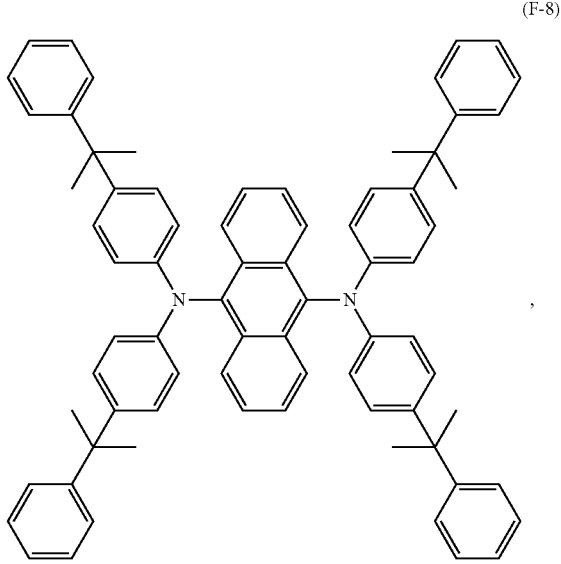 [SMILES: CC(C)(c1ccccc1)c1ccc(N(c2ccc(C(C)(C)c3ccccc3)cc2)c2c3ccccc3c(N(c3ccc(C(C)(C)c4ccccc4)cc3)c3ccc(C(C)(C)c4ccccc4)cc3)c3ccccc23)cc1]
(F-8)

in the light-emitting layer 33, the exciplex formed by the donor molecule of a structure shown by the formula (D-1) and the acceptor molecule of a structure shown by the formula (A-19) is in an amount of 30 wt % with respect to the mass of the light-emitting layer 33, while the fluorescent doping dye of the structure shown by the formula (F-8) is in an amount of 3 wt % with respect to the mass of the light-emitting layer 33.

In the present embodiment, the first electrode 1 of the organic electroluminescent device is made of ITO material, the hole injection layer 31 is made of HATCN, the hole transport layer 32 is made of TAPC, the electron transport layer 34 is made of BPhen, the electron injection layer 35 is made of electron injection material LiF, and the second electrode 2 is made of Al.

The organic electroluminescent device has the following structure:

ITO/HATCN (10 nm)/TAPC (30 nm)/molecule (W-1) (30 nm): molecule (D-1): molecule (A-19): molecule (F-8) (3%)/BPhen (40 nm)/LiF (1 nm)/Al (200 nm).

Wherein, the structure of related materials in this embodiment is shown in the following figure:

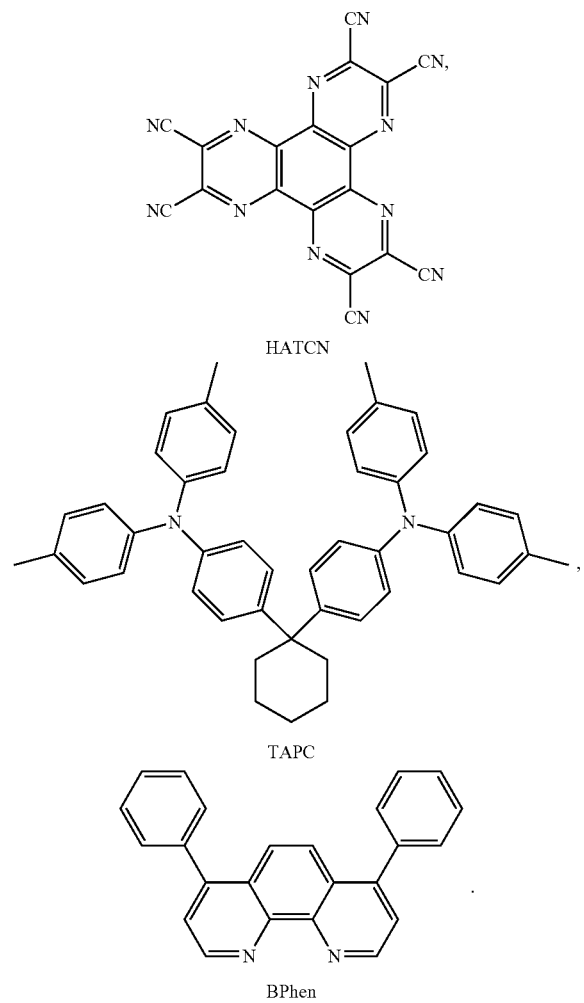

As an alternative embodiment, in the exciplex, the mass ratio of the donor molecule shown by formula (D-1) to the acceptor molecule shown by formula (A-19) may also be selected from other values in the range of 1:9 to 9:1, which can achieve the purpose of the present disclosure and fall within the protection scope of the present disclosure.

As an alternative embodiment, in the light-emitting layer 33, the content of the exciplex formed by the donor molecule shown by the formula (D-1) and the acceptor molecule shown by the formula (A-19) may also be selected from other values in the range of 20 wt % to 50 wt %, the content of the fluorescent doping dye may also be selected from other values in the range of 0.1 wt % to 3 wt %, and the rest are wide band gap materials, which can achieve the purpose of the present disclosure and fall within the protection scope of the present disclosure.

As a further deformation, in the light-emitting layer 33, the content of the exciplex formed by the donor molecule shown by the formula (D-1) and the acceptor molecule shown by the formula (A-19) may also be selected from other values in the range of 5 wt % to 80 wt %, the content of the fluorescent doping dye may also be selected from other values in the range of 0.1 wt % to 10 wt %, and the rest are wide band gap materials, which can achieve the purpose of the present disclosure and fall within the protection scope of the present disclosure.

Embodiment 2

In Embodiment 2, the OLED device may be designed as an organic electroluminescence device having a structure including an anode, a hole injection layer, a hole transport layer, a light-emitting layer, an electron transport layer, an electron injection layer, and the cathode. In this embodiment, a compound containing a fluorenyl is selected as the wide band gap material, and has a structure shown by the formula (W-25):

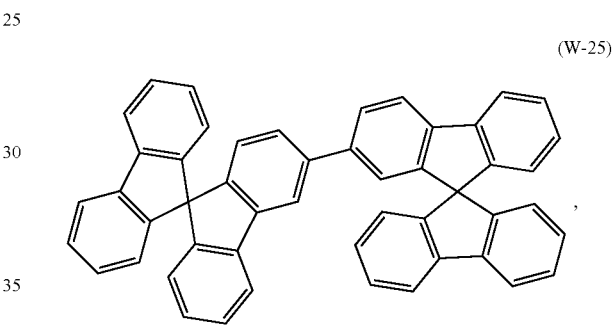

a compound containing a phenyl and a carbazolyl, as represented by the formula (D-1), is selected as the donor molecule:

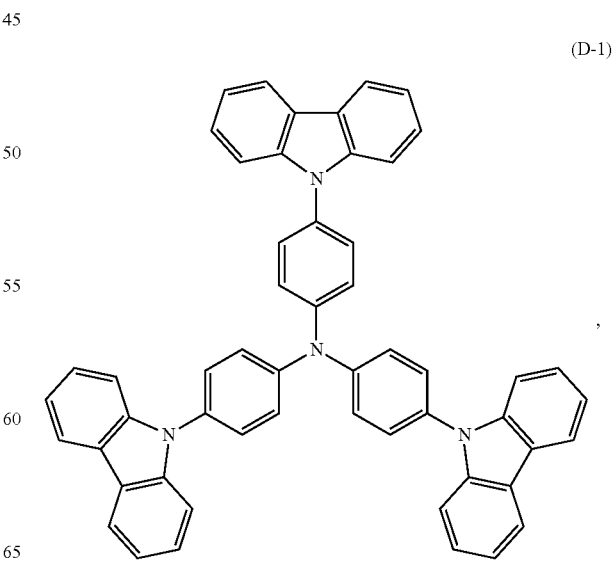

a compound containing a triazine, a phenyl and a diphenylphosphonyl, as represented by the formula (A-6), is selected as the acceptor molecule:

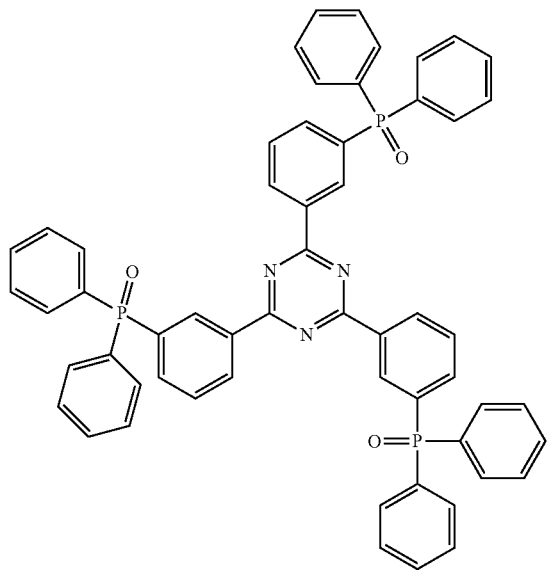

(A-6)

the donor molecule having a structure shown by the formula (D-1) and the acceptor molecule having a structure shown by the formula (A-6) constitute an exciplex, and in the exciplex, the mass ratio of the donor molecule shown by the formula (D)-1 to the acceptor molecule shown by the formula (A-19) is 1:1.

A fluorescent doping dye having a structure shown by the formula (F-11) is selected as the doping material:

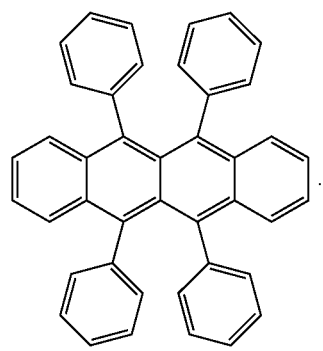

(F-11)

In the light-emitting layer 33, the exciplex formed by the donor molecule having a structure shown by the formula (D-1) and the acceptor molecule having a structure shown by the formula (A-6) is in an amount of 30 wt % with respect to the mass of the light-emitting layer 33, the fluorescent doping dye having a structure shown by the formula (F-11) is in an amount of 1 wt % with respect to the mass of the light-emitting layer 33.

In the embodiment, the first electrode 1 of the organic electroluminescent device is made of ITO material, the hole injection layer 31 is made of HATCN, the hole transport layer 32 is made of TAPC, the electron transport layer 34 is made of TPBI, the electron injection layer 35 is made of LiF, and the electrode 2 is made of Al.

The organic electroluminescent device has the following structure:
ITO/HATCN (10 nm)/TAPC (30 nm)/molecule (W-25) (30 nm): molecule (D-1): molecule (A-6): molecule (F-11) (1%)/TPBI (40 nm)/LiF (1 nm)/Al (200 nm).

Wherein, the structure of related material in this embodiment is shown in the following figure:

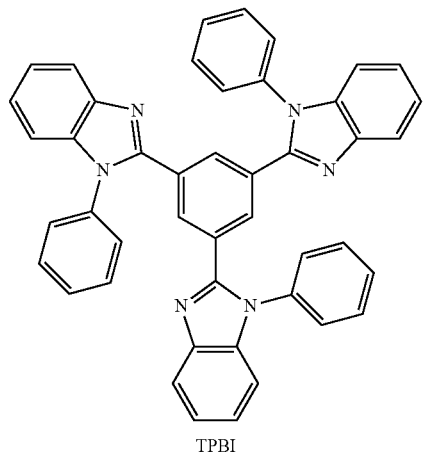

TPBI

Embodiment 3

The present embodiment provides an organic electroluminescent device having the same structure as the structure of the organic electroluminescent device of Embodiment 1. The organic electroluminescent device is different from the organic electroluminescent device provided in Embodiment 1 only in that the hole transport layer is changed from TAPC to NPB, and the NPB has a molecular structure of:

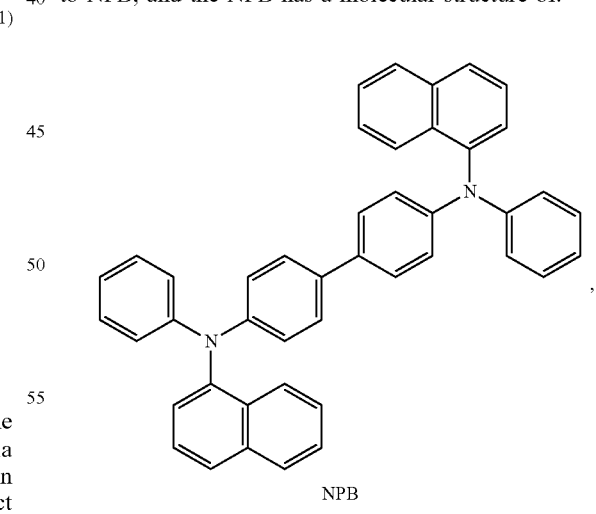

NPB the host material in the light-emitting layer includes a wide band gap material having a structure shown by the formula (W-19) and an exciplex formed by the donor molecule having a structure as shown by the formula (D-2) and the acceptor molecule having a formula as shown in the formula (A-10), the doping material is a fluorescent doping dye having a structure shown by the formula (F-10):

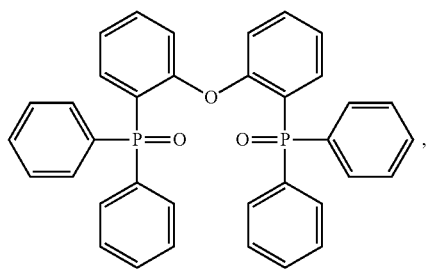
(W-19)

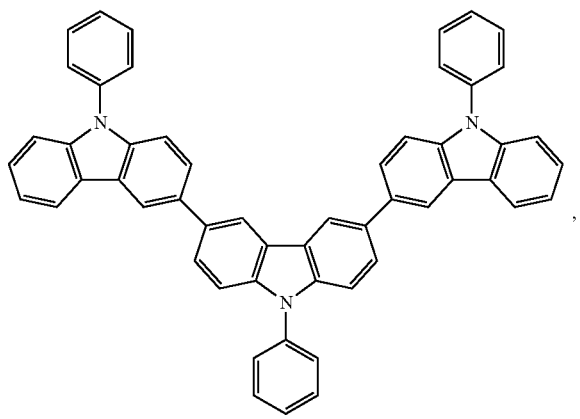
(D-2)

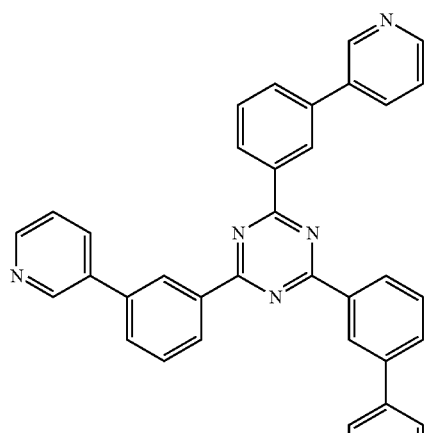
(A-10)

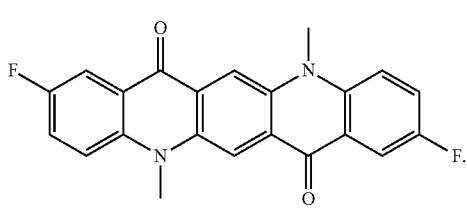
(F-10)

In the light-emitting layer 33, the exciplex formed by the donor molecule having the structure shown by the formula (D-2) and the acceptor molecule having the structure shown by the formula (A-10) is in an amount of 30 wt % with respect to the mass of the light-emitting layer 33, and the fluorescent doping dye having a structure as shown by the formula (F-19) is in an amount of 0.5 wt % with respect to the mass of the light-emitting layer 33.

The organic electroluminescent device has the following structure:

ITO/HATCN (10 nm)/NPB (40 nm)/molecule (W-19): molecule (D-2): molecule (A-10): molecule (F-10) (0.5%, 30 nm)/BPhen (40 nm)/LiF (1 nm)/Al (200 nm).

Comparative Example 1

In the present comparative example, a compound containing a phenyl and a carbazolyl is selected as the donor molecule and has a structure shown by the formula (D-1):

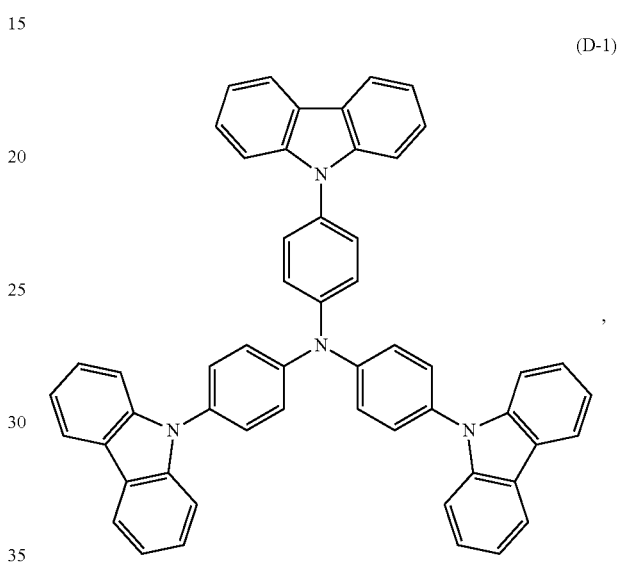
(D-1)

a compound containing a phenyl and a triazinyl, as represented by the formula (A-19), is selected as the acceptor molecule:

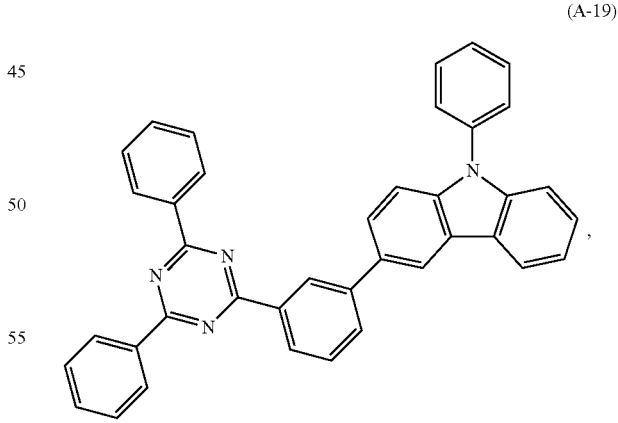
(A-19)

the donor molecule having a structure shown by the formula (D-1) and the acceptor molecule having a structure shown by the formula (A-19) constitute an exciplex, and in the exciplex, the mass ratio of the donor molecule having the structure shown by the formula D-1 to the acceptor molecule having the structure shown by the formula (A-19) is 1:1.

A fluorescent doping dye having a structure shown by the formula (F-8) is selected as the doping material:

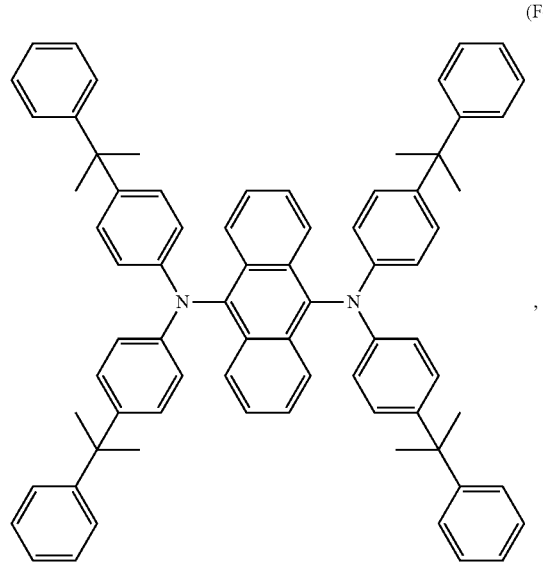

(F-8)

in the light-emitting layer 33, the exciplex formed by the donor molecule having the structure shown by the formula (D-1) and the acceptor molecule having the structure shown by the formula (A-19) is in an amount of 97 wt % with respect to the mass of the light-emitting layer 33, and the fluorescent doping dye having a structure shown by the formula (F-8) is in an amount of 3 wt % with respect to the mass of the light-emitting layer 33.

In the embodiment, the first electrode 1 of the organic electroluminescent device is made of ITO material, the hole injection layer 31 is made of HATCN, the hole transport layer 32 is made of TAPC, the electron transport layer 34 is made of BPhen, the electron injection layer 35 is made of electron injection material LiF, and the second electrode 2 is made of Al.

The organic electroluminescent device has the following structure:
ITO/HATCN (10 nm)/TAPC (30 nm)/molecule (D-1): molecule (A-19): molecule (F-8) (3%)/BPhen (40 nm)/LiF (1 nm)/Al (200 nm).

Embodiment 4

The present embodiment differs from Embodiment 1 in that the doping material in the light-emitting layer 33 is selected to have a structure as shown by the formula (F-5). Wherein, in the light-emitting layer 33, the mass fraction of the exciplex is 30%, and the mass fraction of the fluorescent doping dye is 3%. The device has a driving voltage of 4.21V, a chromaticity coordinate of (0.36, 0.57), an external quantum efficiency of 18.1%, and a roll-off of 4.54% at a luminance of 5000 cd/m$^2$.

Embodiment 5

The present embodiment differs from Embodiment 1 in that: the host material in the light-emitting layer 33 includes a wide band gap material having a structure shown by the formula (W-4) and an exciplex formed by the donor molecule shown by the formula (D-17) and the acceptor molecule shown by the formula (A-32); the doping material is selected to have a structure shown by the formula (F-6). Wherein, in the exciplex, the mass ratio of the donor molecule to the acceptor molecule is 2:1; in the light-emitting layer 33, the mass fraction of the exciplex is 27%, and the mass fraction of the fluorescent doping dye is 10%. The device has a driving voltage of 4.02 V, a chromaticity coordinate of (0.37, 0.58), an external quantum efficiency of 18.5%, and a roll-off of 3.83% at a luminance of 5000 cd/m$^2$.

Embodiment 6

The present embodiment differs from Embodiment 1 in that: the host material in the light-emitting layer 33 includes a wide band gap material having a structure shown by the formula (W-15) and an exciplex formed by the donor molecule shown by the formula (D-8) and the acceptor molecule shown by the formula (A-28); the doping material is selected to have a structure shown by the formula (F-7). Wherein, in the exciplex, the mass ratio of the donor molecule to the acceptor molecule is 1:7; in the light-emitting layer 33, the mass fraction of the exciplex is 57%, and the mass fraction of the fluorescent doping dye is 4%. The device has a driving voltage of 4.15V, a chromaticity coordinate of (0.36, 0.58), an external quantum efficiency of 17.8%, and a roll-off of 4.58% at a luminance of 5000 cd/m$^2$.

Embodiment 7

The present embodiment differs from Embodiment 1 in that: the host material in the light-emitting layer 33 includes a wide band gap material having a structure shown by the formula (W-21) and an exciplex formed by the donor molecule shown by the formula (D-14) and the acceptor molecule shown by the formula (A-15); the doping material is selected to have a structure shown by the formula (F-11). Wherein, in the exciplex, the mass ratio of the donor molecule to the acceptor molecule is 4:7; in the light-emitting layer 33, the mass fraction of the exciplex is 68%, and the mass fraction of the fluorescent doping dye is 0.1%. The device has a driving voltage of 3.98V, a chromaticity coordinate of (0.49, 0.50), an external quantum efficiency of 15.6%, and a roll-off of 4.36% at a luminance of 5000 cd/m$^2$.

Embodiment 8

The present embodiment differs from Embodiment 1 in that: the host material in the light-emitting layer 33 includes a wide band gap material having a structure shown by the formula (W-40) and an exciplex formed by donor molecule shown by the formula (D-10) and acceptor molecule shown by the formula (A-7); the doping material is selected to have a structure shown by the formula (F-6). Wherein, in the exciplex, the mass ratio of the donor molecule to the acceptor molecule is 9:2; in the light-emitting layer 33, the mass fraction of the exciplex is 80%, and the mass fraction of the fluorescent doping dye is 1.5%. The device has a driving voltage of 4.26V, a chromaticity coordinate of (0.37, 0.58), an external quantum efficiency of 18.5%, and a roll-off of 7.87% at a luminance of 5000 cd/m$^2$.

Embodiment 9

The present embodiment differs from Embodiment 1 in that: the host material in the light-emitting layer 33 includes a wide band gap material having a structure shown by the formula (W-6) and an exciplex formed by the donor molecule shown by the formula (D-19) and the acceptor molecule shown by the formula (A-2); the doping material is selected to have a structure shown by the formula (F-9). Wherein, in the exciplex, the mass ratio of the donor molecule to the acceptor molecule is 8:3; in the light-emitting layer 33, the mass fraction of the exciplex is 5%, and the mass fraction of the fluorescent doping dye is 1%. The device has a driving voltage of 4.31V, a chromaticity coordinate of (0.44, 0.45), an external quantum efficiency of 16.7%, and a roll-off of 6.52% at a luminance of 5000 cd/m$^2$.

Embodiment 10

The present embodiment differs from Embodiment 1 in that: the host material in the light-emitting layer 33 includes a wide band gap material having a structure shown by the formula (W-28) and an exciplex formed by the donor molecule shown by the formula (D-15) and the acceptor molecule shown by the formula (A-13); the doping material is selected to have a structure shown by the formula (F-10). Wherein, in the exciplex, the mass ratio of the donor molecule to the acceptor molecule is 4:1; in the light-emitting layer 33, the mass fraction of the exciplex is 11%, and the mass fraction of the fluorescent doping dye is 2.8%. The device has a driving voltage of 4.40V, a chromaticity coordinate of (0.45, 0.45), an external quantum efficiency of 16.9%, and a roll-off of 6.61% at a luminance of 5000 cd/m$^2$.

Embodiment 11

The present embodiment differs from Embodiment 1 in that: the host material in the light-emitting layer 33 includes a wide band gap material having a structure shown by the formula (W-32) and an exciplex formed by the donor molecule shown by the formula (D-16) and the acceptor molecule shown by the formula (A-18); the doping material is selected to have a structure shown by the formula (F-8). Wherein, in the exciplex, the mass ratio of the donor molecule to the acceptor molecule is 3:7; in the light-emitting layer 33, the mass fraction of the exciplex is 20%, and the mass fraction of the fluorescent doping dye is 7%. The device has a driving voltage of 4.23V, a chromaticity coordinate of (0.36, 0.58), an external quantum efficiency of 18.8%, and a roll-off of 5.56% at a luminance of 5000 cd/m$^2$.

Embodiment 12

The present embodiment differs from Embodiment 1 in that: the host material in the light-emitting layer 33 includes a wide band gap material having a structure shown by the formula (W-14) and an exciplex formed by the donor molecule shown by the formula (D-12) and the acceptor molecule shown by the formula (A-27); the doping material is selected to have a structure shown by the formula (F-10). Wherein, in the exciplex, the mass ratio of the donor molecule to the acceptor molecule is 1:1; in the light-emitting layer 33, the mass fraction of the exciplex is 50%, and the mass fraction of the fluorescent doping dye is 5%. The device has a driving voltage of 4.52V, a chromaticity coordinate of (0.44, 0.45), an external quantum efficiency of 17.8%, and a roll-off of 7.10% at a luminance of 5000 cd/m$^2$.

Embodiment 13

The present embodiment differs from Embodiment 1 in that: the host material in the light-emitting layer 33 includes a wide band gap material having a structure shown by the formula (W-8) and an exciplex formed by the donor molecule shown by the formula (D-4) and the acceptor molecule shown by the formula (A-28); the doping material is selected to have a structure shown by the formula (F-11). Wherein, in the exciplex, the mass ratio of the donor molecule to the acceptor molecule is 8:1; in the light-emitting layer 33, the mass fraction of the exciplex is 18%, and the mass fraction of the fluorescent doping dye is 9%. The device has a driving voltage of 4.56V, a chromaticity coordinate of (049, 0.50), an external quantum efficiency of 16.6%, and a roll-off of 6.23% at a luminance of 5000 cd/m$^2$.

Embodiment 14

The present embodiment differs from Embodiment 1 in that: the host material in the light-emitting layer 33 includes a wide band gap material having a structure shown by the formula (W-17) and an exciplex formed by the donor molecule shown by the formula (D-6) and the acceptor molecule shown by the formula (A-31); the doping material is selected to have a structure shown by the formula (F-19). Wherein, in the exciplex, the mass ratio of the donor molecule to the acceptor molecule is 5:1; in the light-emitting layer 33, the mass fraction of the exciplex is 65%, and the mass fraction of the fluorescent doping dye is 5%. The device has a driving voltage of 4.12V, a chromaticity coordinate of (059, 0.40), an external quantum efficiency of 15.5%, and a roll-off of 7.12% at a luminance of 5000 cd/m$^2$.

Embodiment 15

The present embodiment differs from Embodiment 1 in that: the host material in the light-emitting layer 33 includes a wide band gap material having a structure shown by the formula (W-22) and an exciplex formed by donor molecule shown by the formula (D-3) and acceptor molecule shown by the formula (A-16); the doping material is selected to have a structure shown by the formula (F-20). Wherein, in the exciplex, the mass ratio of the donor molecule to the acceptor molecule is 7:2; in the light-emitting layer 33, the mass fraction of the exciplex is 45%, and the mass fraction of the fluorescent doping dye is 2.5%. The device has a driving voltage of 4.23V, a chromaticity coordinate of (059, 0.41), an external quantum efficiency of 14.5%, and a roll-off of 5.76% at a luminance of 5000 cd/m$^2$.

Embodiment 16

The present embodiment differs from Embodiment 1 in that: the host material in the light-emitting layer 33 includes a wide band gap material having a structure shown by the formula (W-37) and an exciplex formed by the donor molecule shown by the formula (D-11) and the acceptor molecule shown by the formula (A-33); the doping material is selected to have a structure shown by the formula (F-20). Wherein, in the exciplex, the mass ratio of the donor molecule to the acceptor molecule is 1:2; in the light-emitting layer 33, the mass fraction of the exciplex is 25%, and the mass fraction of the fluorescent doping dye is 1.8%. The device has a driving voltage of 4.31V, a chromaticity coordinate of (059, 0.41), an external quantum efficiency of 14.6%, and a roll-off of 6.78% at a luminance of 5000 cd/m$^2$.

As an alternative embodiment, in the above embodiments, the wide band gap material may be replaced with a compound having a structure shown by any one of the formulas (W-1) to (W-40).

As an alternative embodiment, in the above embodiments, the donor molecule may be replaced with a compound having a structure shown by any one of the formulas (D-1) to (D-19).

As an alternative embodiment, in the above embodiments, the acceptor molecule may be replaced with a compound having a structure shown by any one of the formulas (A-1) to (A-33).

As an alternative embodiment, in the above embodiments, the fluorescent doping dye may be replaced with a compound having a structure shown by any one of the formulas (F-1) to (F-24).

As an alternative embodiment, in the above embodiments, the mass ratio of the donor molecule to the acceptor molecule may be any ratio ranging from 1:9 to 9:1, as a preferred embodiment, in the above embodiments, the mass ratio of the donor molecule to the acceptor molecule may be any ratio ranging from 1:5 to 5:1.

As an alternative embodiment, in the above embodiments, the doping ratio of the exciplex may be any value ranging from 5 wt % to 80 wt %; the doping ratio of the fluorescent doping dye may be any value ranging from 0.1 wt % to 10 wt %.

Test Example 1

The characteristics of the devices in Embodiments 1-3 and Comparative Example 1, such as the voltage, luminance, efficiency, and luminescence spectra, etc., were tested. The test results are shown in the following table:

TABLE 1

Performance test of OLED devices

|  | Driving voltage/ V at luminance 5000 cd/m$^2$ | Chromaticity coordinate CIE (x, y) | External quantum efficiency at 5000 cd/m$^2$ | External quantum efficiency at 10000 cd/m$^2$ | roll-off |
|---|---|---|---|---|---|
| Embodiment 1 | 4.25 | (0.36, 0.57) | 18.16 | 17.60 | 3.08% |
| Embodiment 2 | 4.32 | (0.49, 0.50) | 14.20 | 13.71 | 3.52% |
| Embodiment 3 | 4.16 | (0.44, 0.45) | 16.1 | 15.3 | 4.97% |
| Comparative Example 1 | 4.85 | (0.36, 0.58) | 11.40 | 10.34 | 9.65% |

Figure 2:
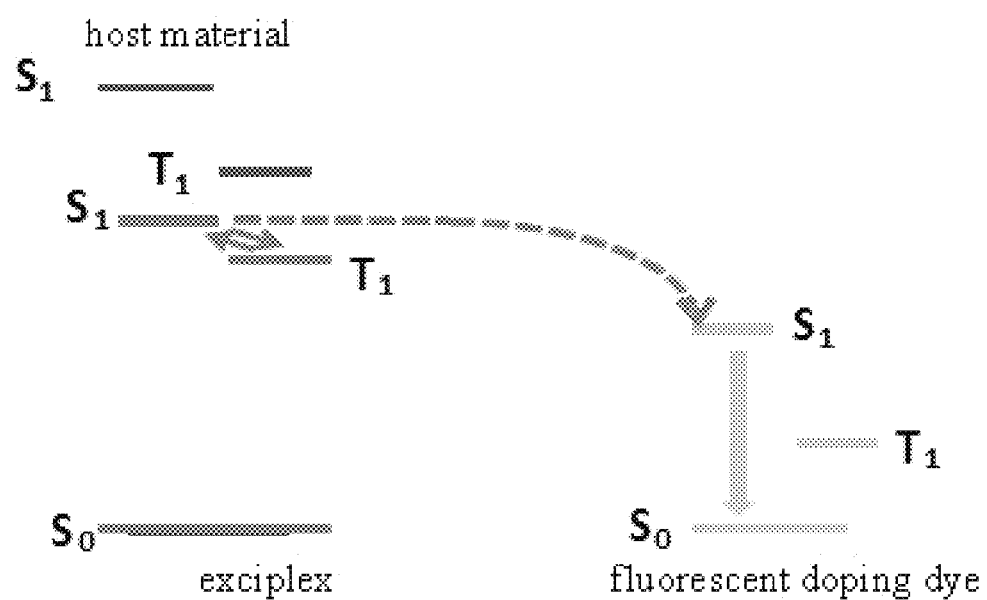
FIG. 2 is a schematic diagram of energy transfer in the light-emitting process of an organic electroluminescent device of the present disclosure.

As can be seen from Table 1, in the OLED devices prepared using the materials provided in Embodiments 1-3 and Comparative Example 1, the driving voltage, external quantum efficiency, and roll-off of the OLED devices of Embodiments 1-3 were superior to that of the OLED device of Comparative Example 1. This is due to the introduction of the band gap host material in the light-emitting layer provided in Embodiments 1-3, which increases the distance between the donor molecule and the acceptor molecule, and reduces the degree of overlap between the HOMO and LUMO of the formed exciplex host, reduces the singlet-triplet energy level difference ΔEST, thereby increasing the reverse intersystem crossing rate ($k_{RISC}$) of the exciplex, and the excitons are easily returned from the triplet to the singlet through the reverse intersystem crossing process, greatly improving the utilization of excitons; at the same time, it also suppresses the Dexter energy transfer and improves the luminous efficiency of the device, as shown in FIG. 2.

The introduction of the wide band gap material increases the distance between the donor molecule and the acceptor molecule in the exciplex, reduces the triplet exciton concentration in the light-emitting layer, and suppresses the triplet-triplet annihilation (TTA) and the triplet-polaron annihilation (TPA), helps to reduce the roll-off of the device efficiency and increase the lifetime of the electroluminescent device.

Figure 3:
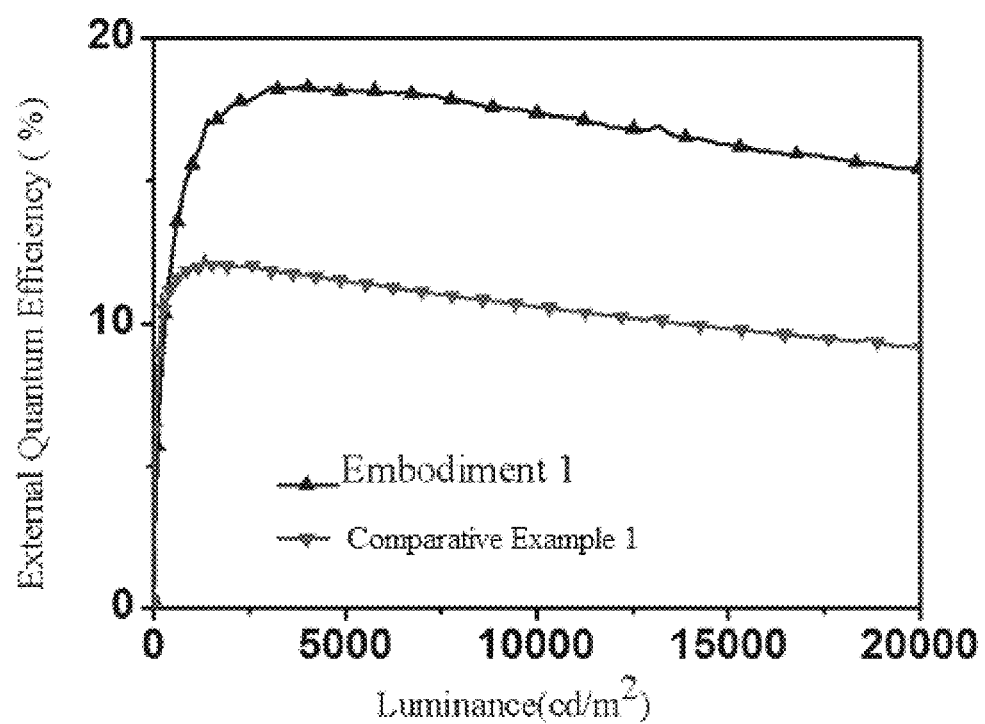
FIG. 3 is a comparison of external quantum efficiency of the organic electroluminescent devices of Embodiment 1 and Comparative Example 1 of the present disclosure.
Figure 4:
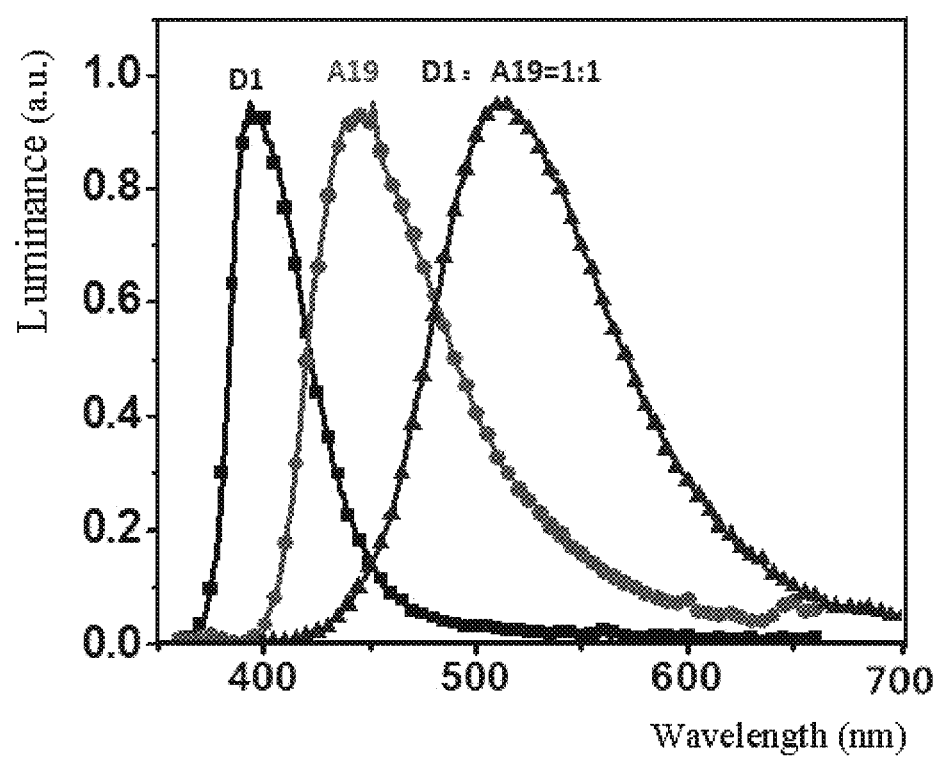
FIG. 4 is a spectrum of an exciplex formed by the donor molecule and the acceptor molecule in Embodiment 1 of the present disclosure.
Figure 5:
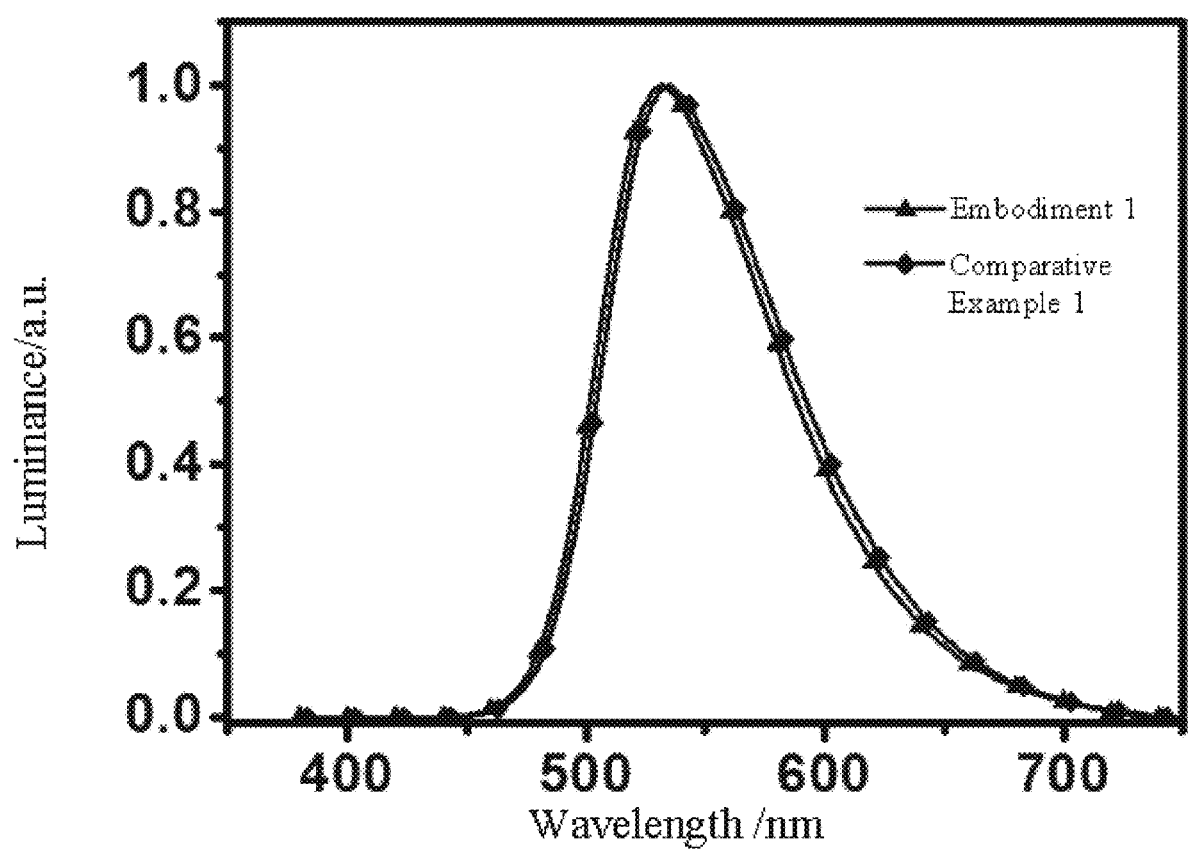
FIG. 5 is electroluminescence spectra of Embodiment 1 and Comparative Example 1 of the present disclosure.

As shown in FIG. 3, the ordinate is the external quantum efficiency and the abscissa is the luminance. The electroluminescence performance of the OLED device of Embodiment 1 is better than that of the OLED device of Comparative Example 1 at the same luminance, which shows that the performance of the device with introducing a wide band gap material is better than that of the device without a wide bandgap material, exhibited by external quantum efficiency; as shown in FIG. 4, the photoluminescence spectrum with the donor and the acceptor doped has a wider half-width and a significant red shift compared to the corresponding donor and acceptor molecules, which confirms the production of the exciplex; the luminescence spectra of the organic electroluminescent devices of Embodiment 1 and Comparative Example 1 are shown in FIG. 5.

It is apparent that the above-described embodiments are merely examples for clear descriptions, but not intended to limit the implementations. Other changes or variations of the various forms may be made by those skilled in the art based on the above description. There is no need and no way to exhaust all of the implementations. Obvious changes or variations resulting therefrom are still within the scope of the application.

The invention claimed is:

1. An organic electroluminescent device, comprising: a light-emitting layer, the light-emitting layer comprising a host material and a guest material, the host material comprising a wide band gap material and an exciplex, the exciplex composed of and formed by a donor molecule and an acceptor molecule, wherein the wide band gap material is a compound containing a carbazolyl and an aryl, wherein the guest material is a fluorescent doping dye, wherein the donor molecule is a compound having hole transport property, wherein the acceptor molecule is a compound having electron transport property, wherein a mass ratio of the wide band gap material to the exciplex is between 1:19 to 4:1, and wherein in the exciplex, a mass ratio of the donor molecule to the acceptor molecule is between 1:9 and 9:1.

2. The organic electroluminescent device of claim 1, wherein a triplet energy level of the wide band gap material is higher than a singlet energy level of the exciplex.

3. The organic electroluminescent device of claim 1, wherein a triplet level of the donor molecule and a triplet level of the acceptor molecule are respectively higher than a triplet level of the exciplex.

4. The organic electroluminescent device of claim 1, wherein an energy level difference between a singlet level and a triplet level of the exciplex is less than 0.15 eV.
5. The organic electroluminescent device of claim 1, wherein the wide band gap material is selected from at least one of compounds of structures shown below:
(W-1)
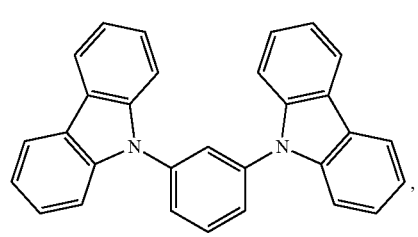
(W-2)
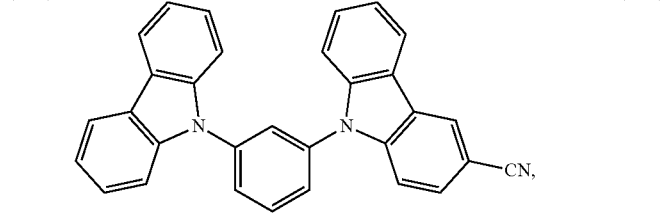
(W-3)
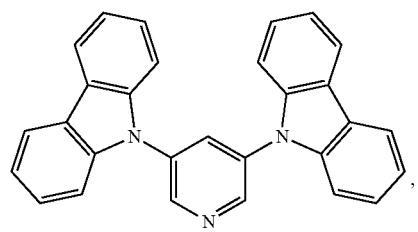
(W-4)
(W-5)
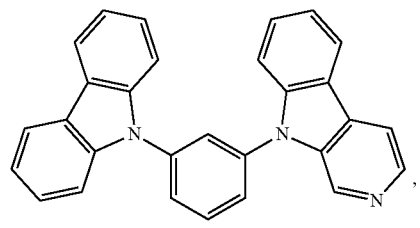
(W-6)
(W-7)
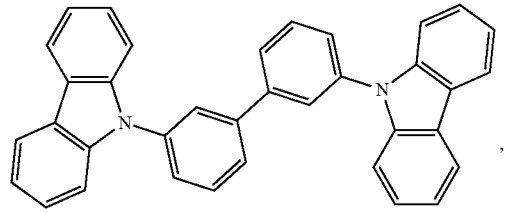
(W-8)
(W-10)
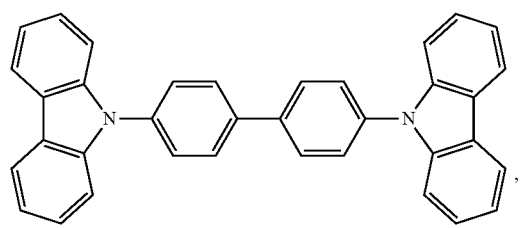
(W-11)
(W-13)
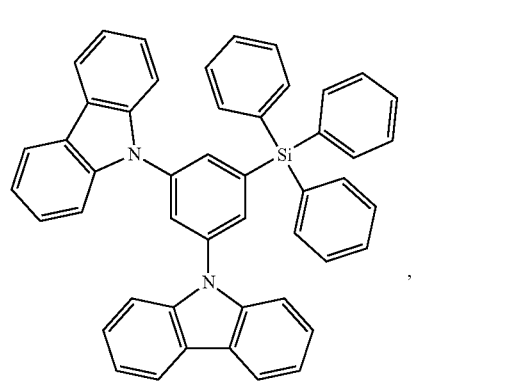
(W-14)
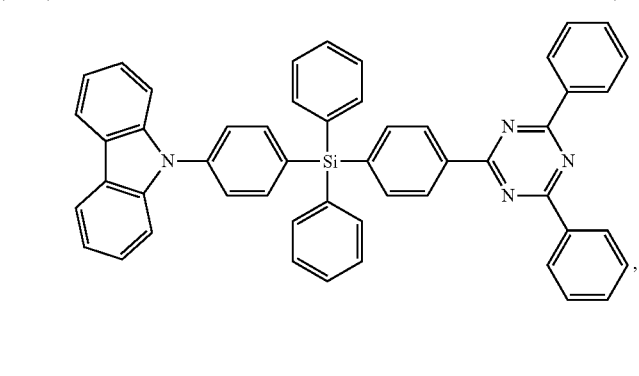

-continued
(W-16)
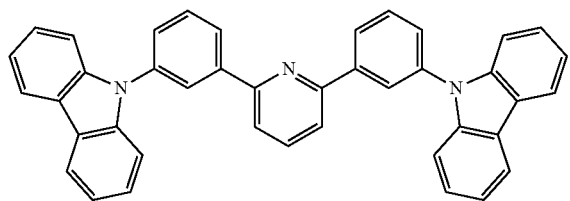
(W-24)
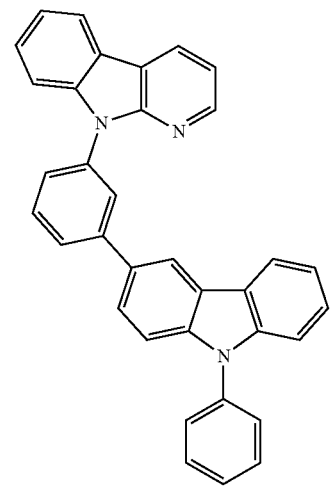
(W-26)
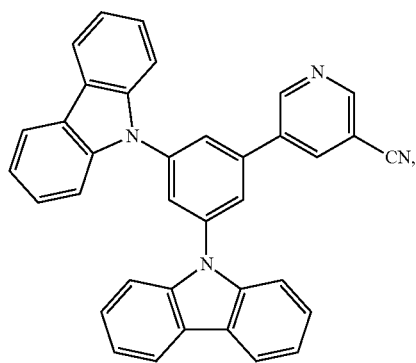
(W-27)
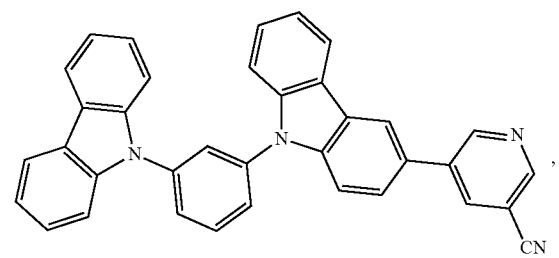
(W-28)
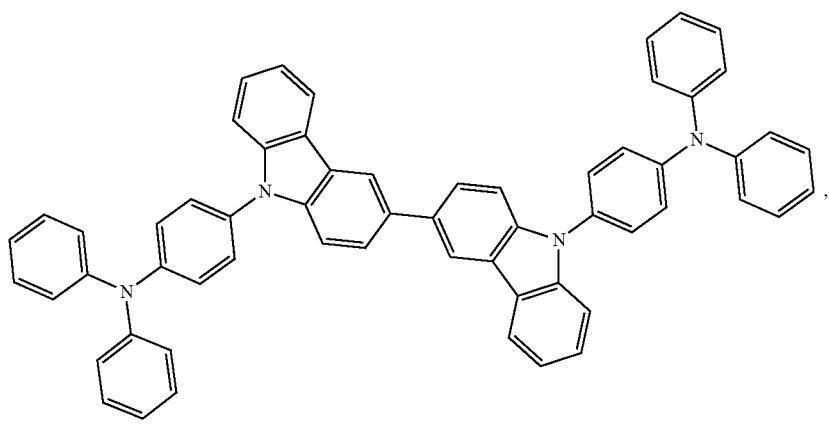

-continued
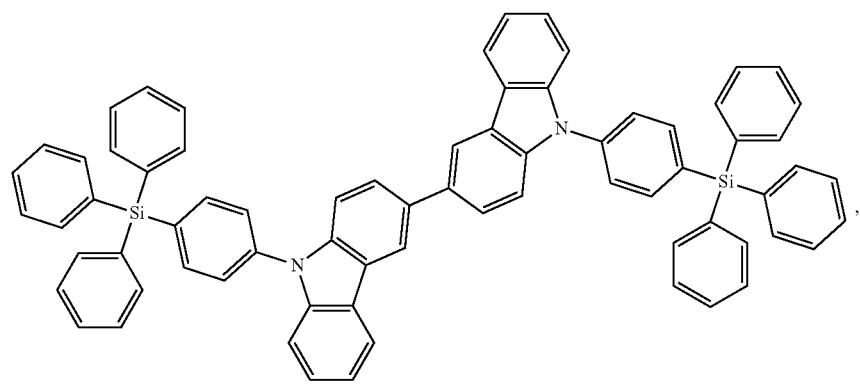
(W-29)
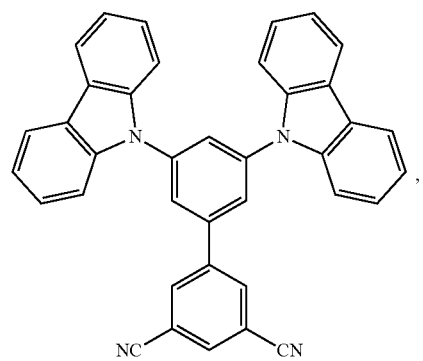
(W-31)
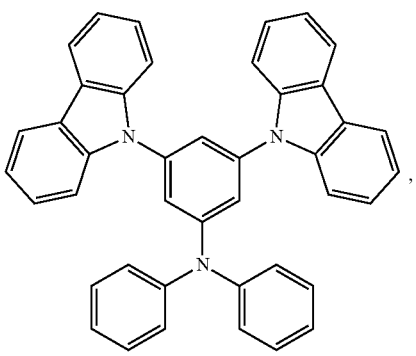
(W-32)
6. The organic electroluminescent device of claim 1, wherein the donor molecule is a compound containing at least one of a carbazolyl, a triphenylamine, and an aryl.
7. The organic electroluminescent device of claim 6, wherein the donor molecule is selected from at least one of compounds of structures shown below:
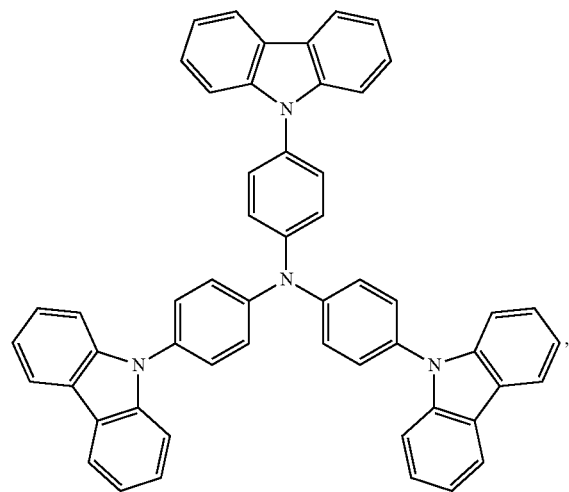
(D-1)
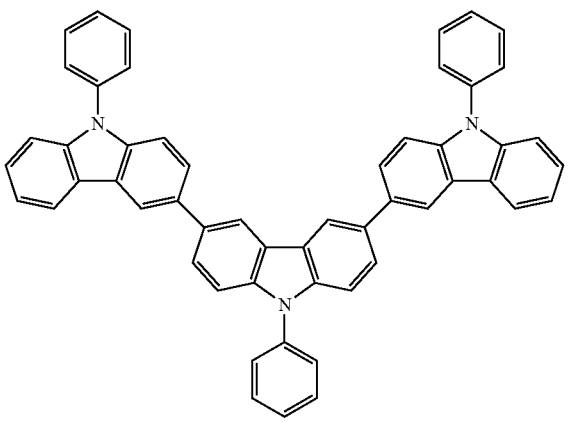
(D-2)

-continued
(D-3)
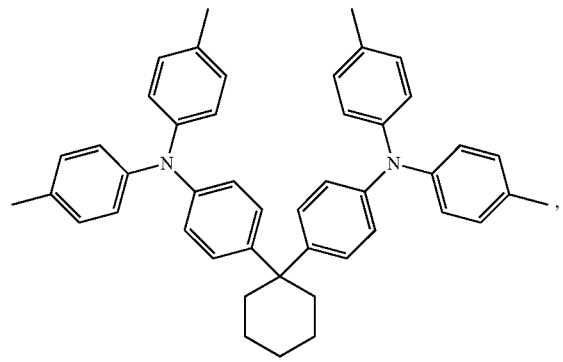
(D-4)
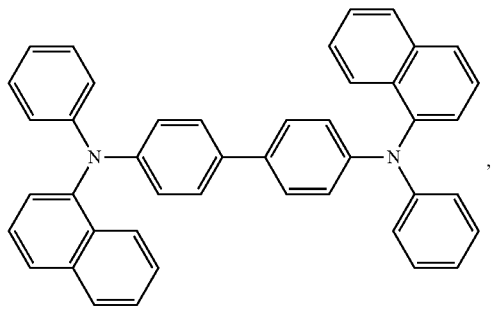
(D-5)
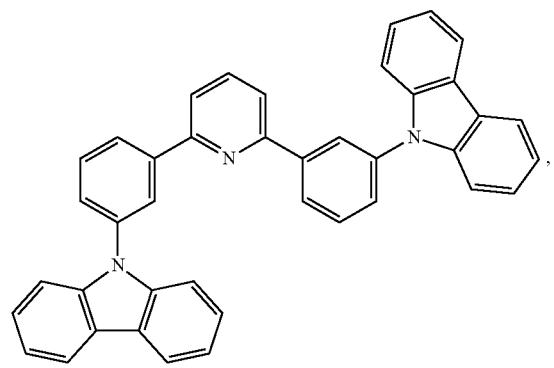
(D-6)
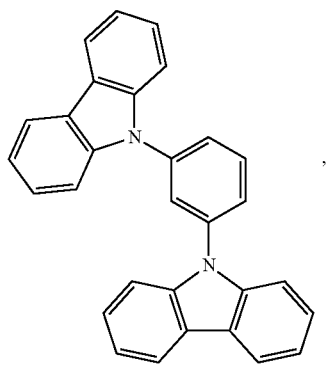
(D-7)
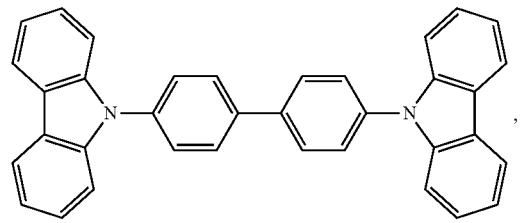
(D-8)
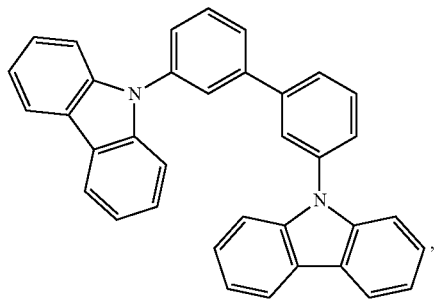
(D-9)
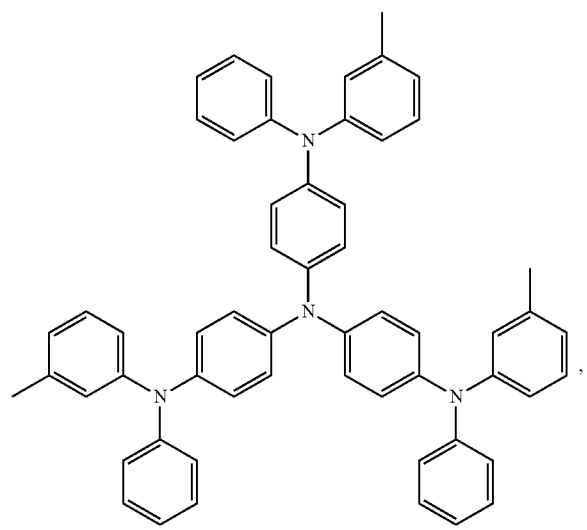
(D-10)
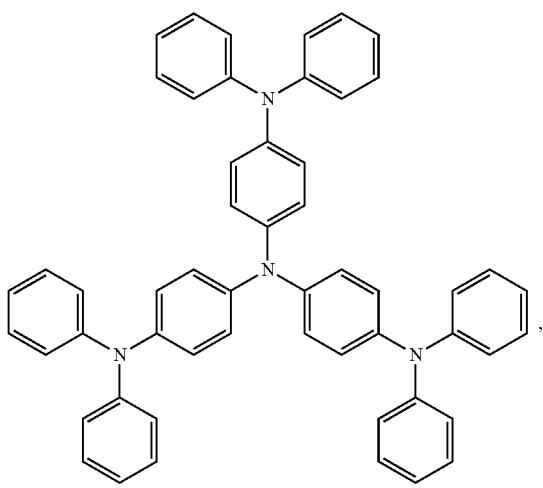

-continued
(D-11)
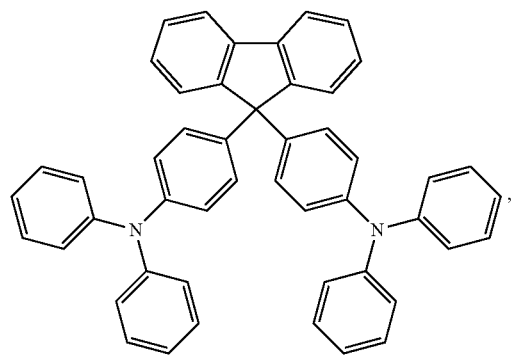
(D-12)
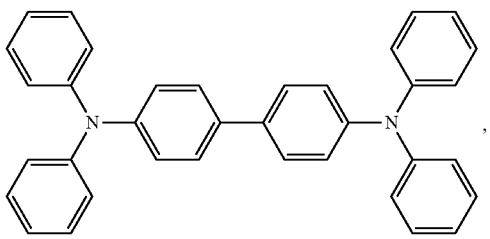
(D-13)
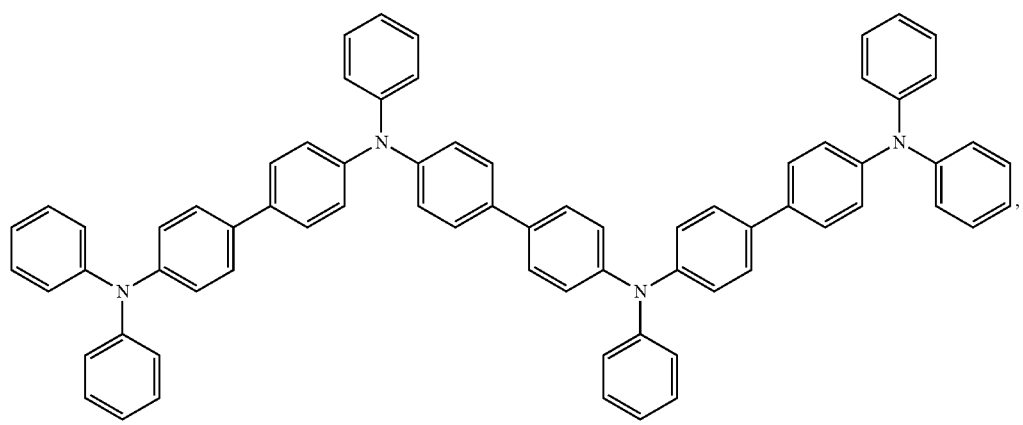
(D-14)
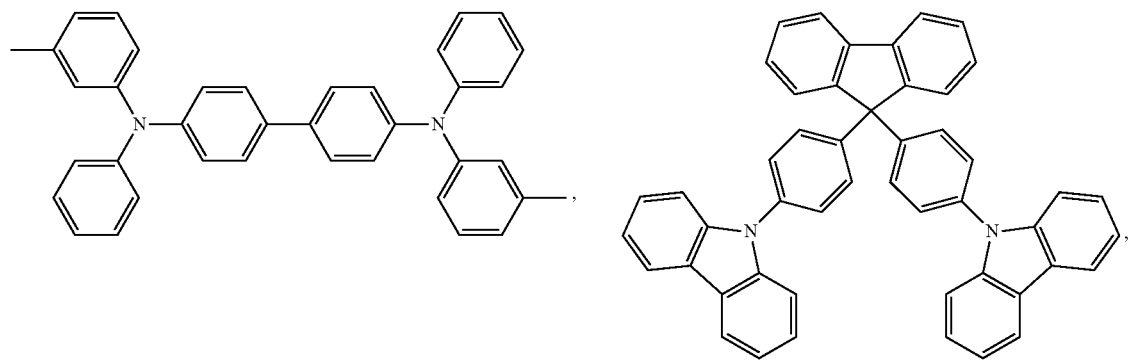
(D-15)
(D-16)
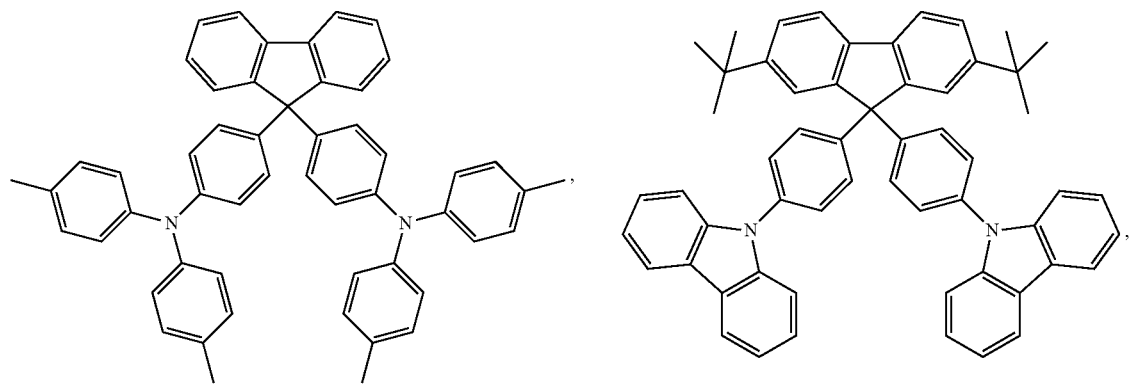
(D-17)

-continued

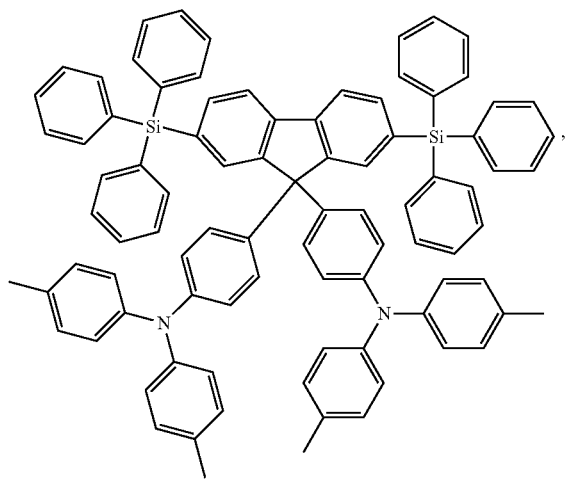
(D-18)

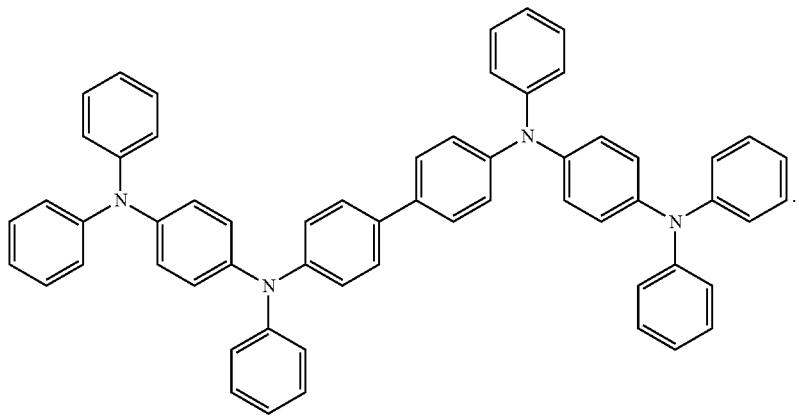
(D-19)

8. The organic electroluminescent device of claim 1, wherein the acceptor molecule is a compound containing at least one of a pyridyl, a pyrimidinyl, a triazinyl, a carbazolyl, an aryl, a cyano, and a diphenylphosphono.

9. The organic electroluminescent device of claim 8, wherein the acceptor molecule is selected from at least one of compounds of structures shown below:

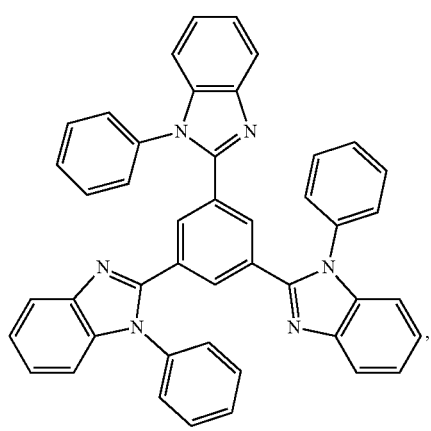
(A-1)

-continued

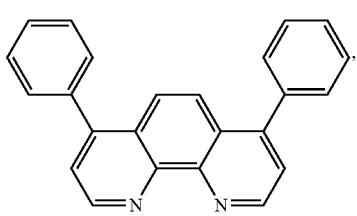
(A-2)

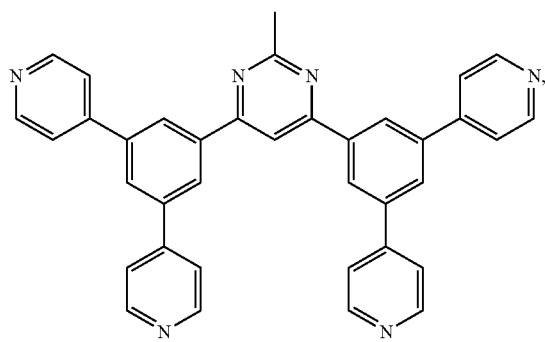
(A-3)

(A-4)
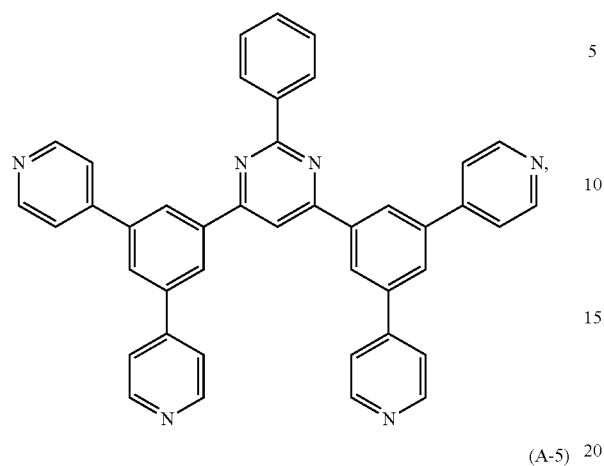
(A-5)
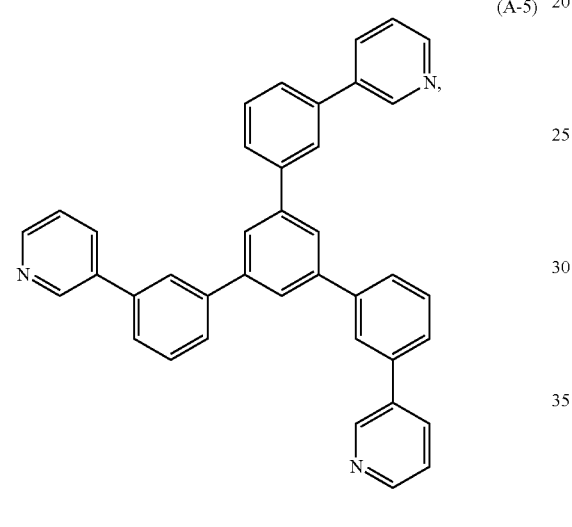
(A-6)
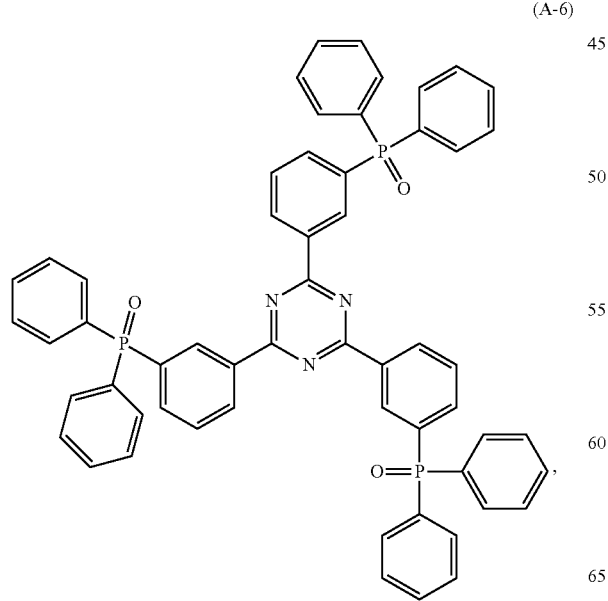
(A-7)
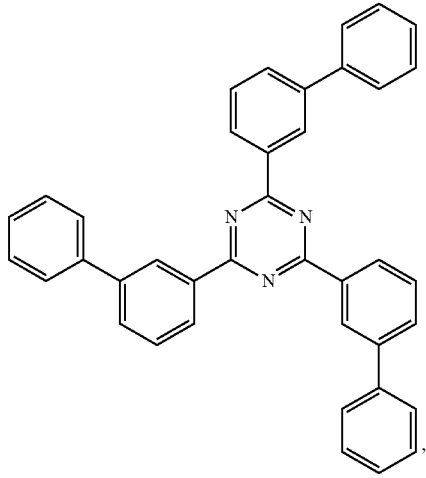
(A-8)
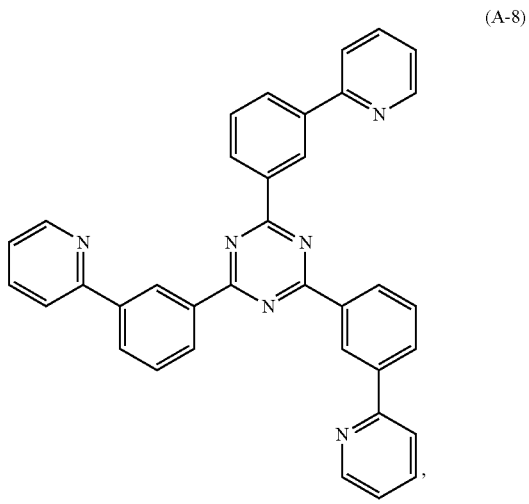
(A-9)
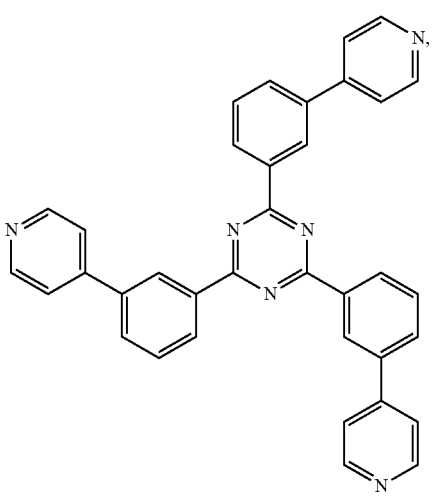

(A-10)
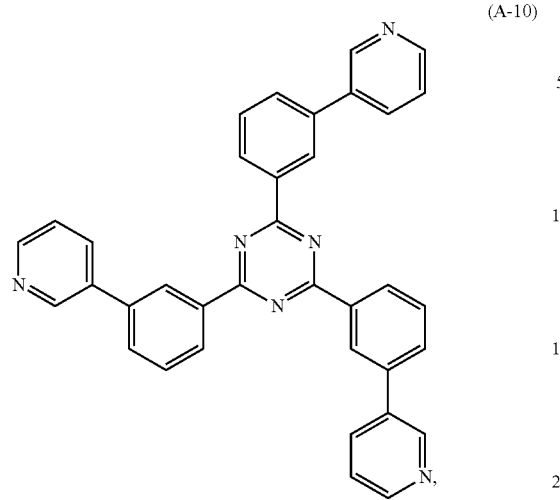
(A-11)
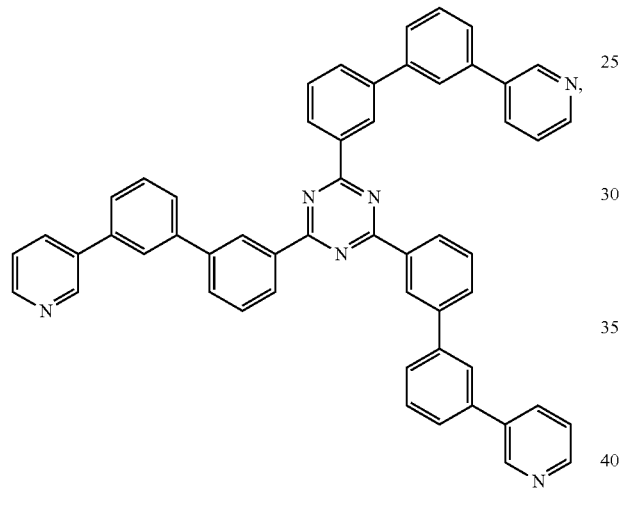
(A-12)
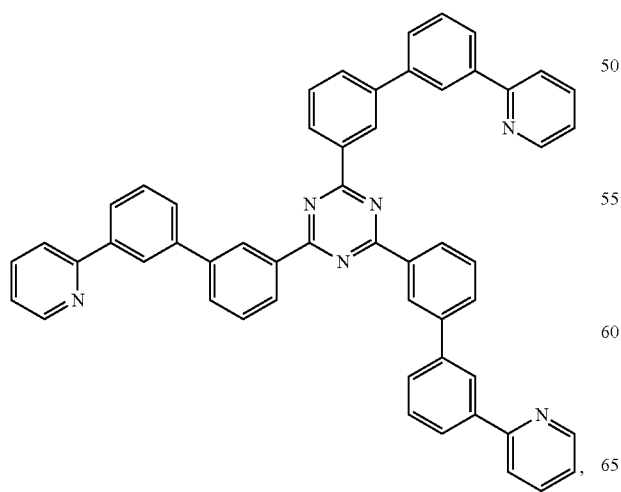
(A-13)
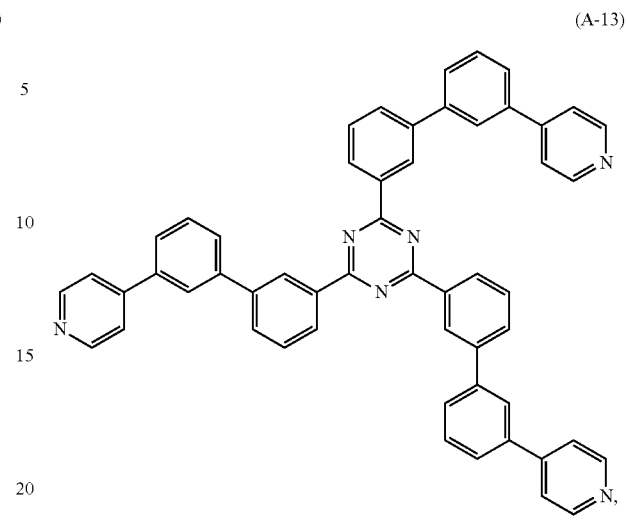
(A-14)
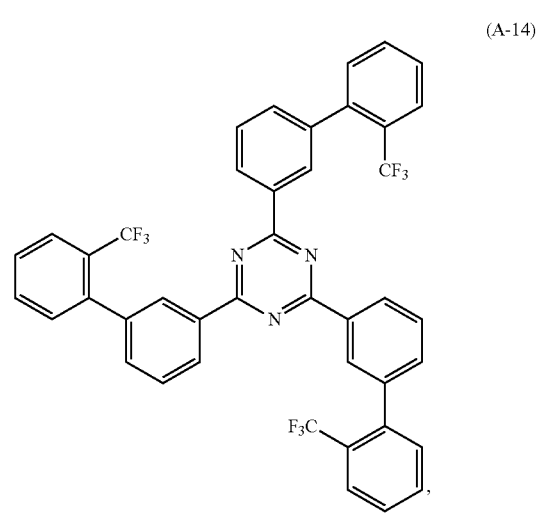
(A-15)
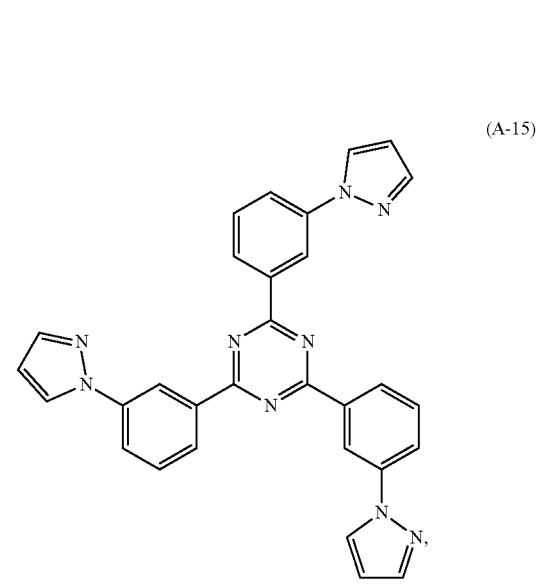

(A-16)
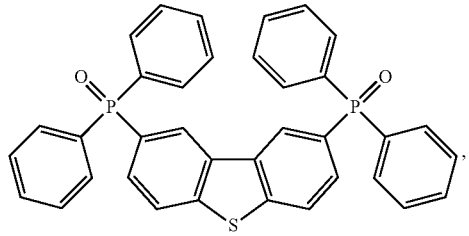
(A-17)
(A-18)
(A-19)
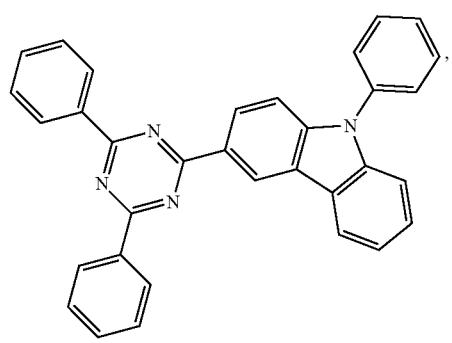
(A-20)
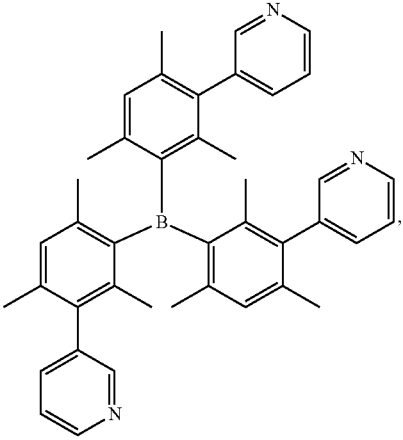
(A-21)
(A-22)
(A-23)
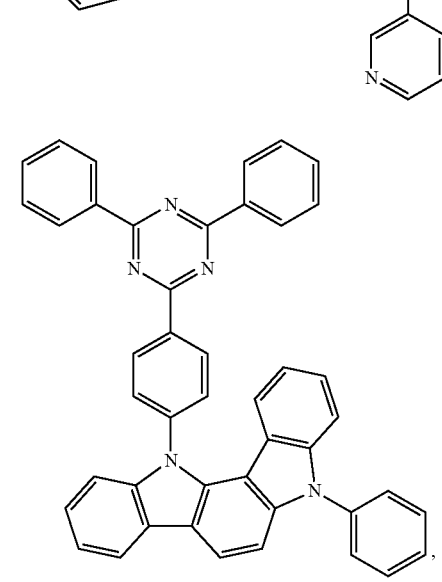

(A-24)
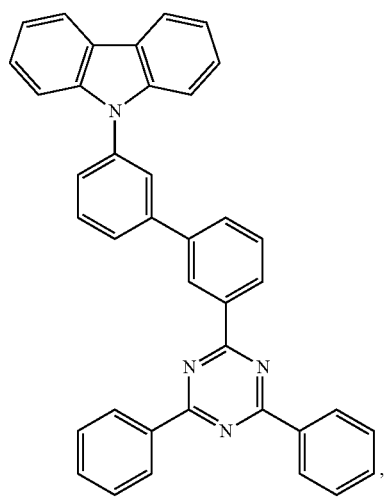
(A-25)
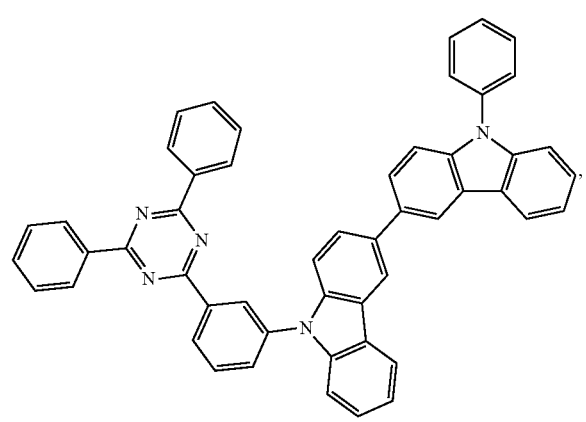
(A-26)
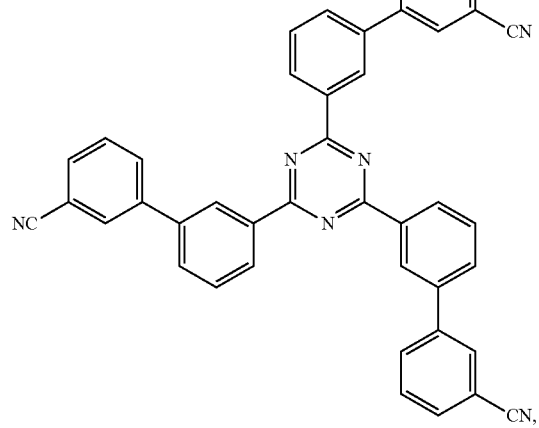
(A-27)
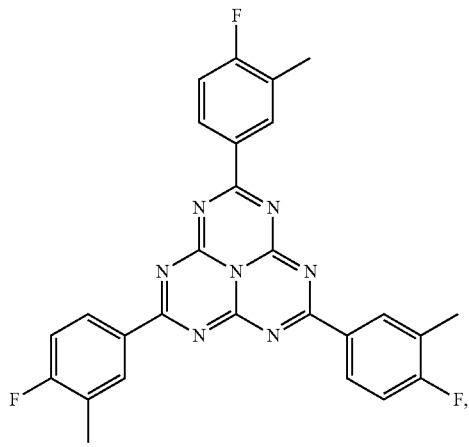
(A-28)
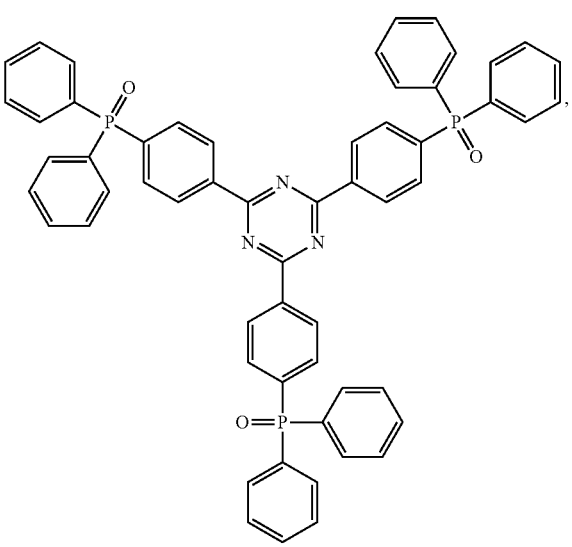
(A-29)
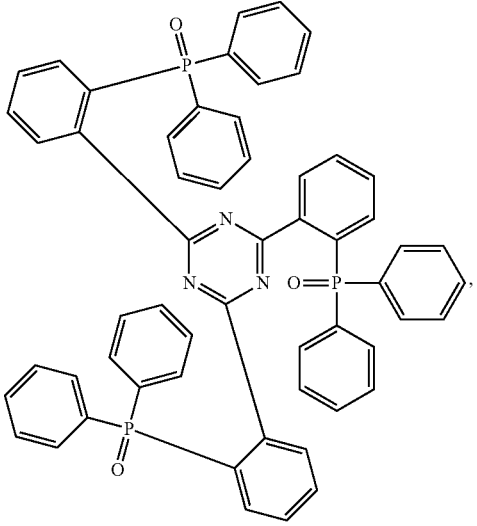

-continued
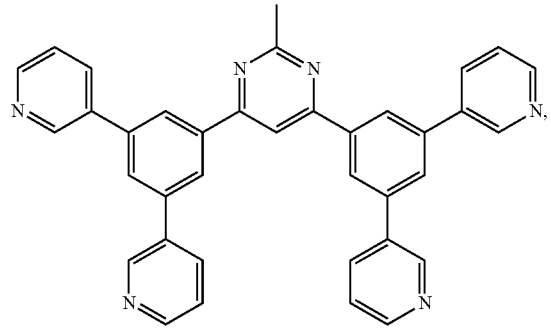
(A-30)
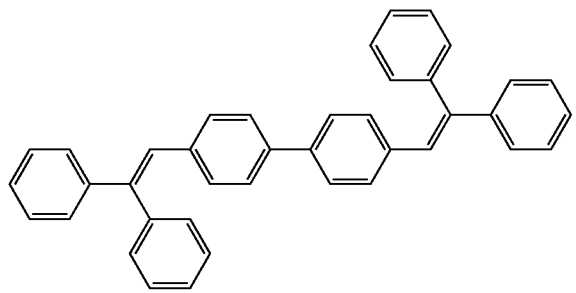
(A-31)
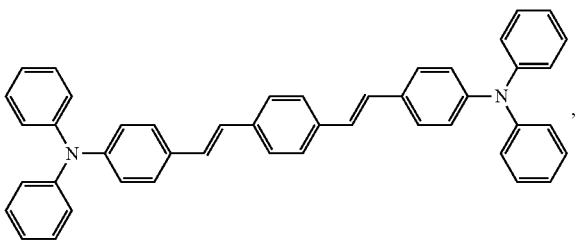
(A-32)
(A-33)
10. The organic electroluminescent device of claim 1, wherein the fluorescent doping dye is selected from at least one of compounds of structures shown below:
(F-1)
(F-2)
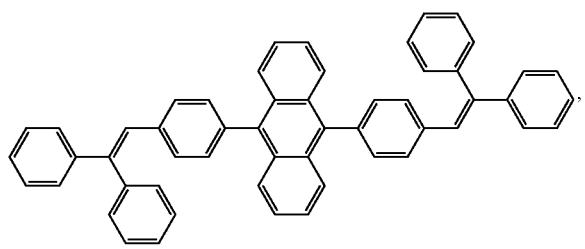
(F-3)
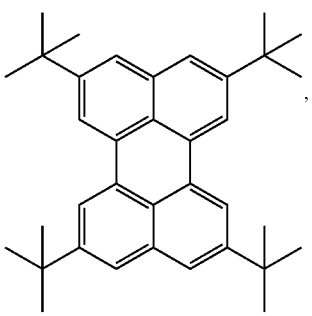
(F-4)

(F-5)
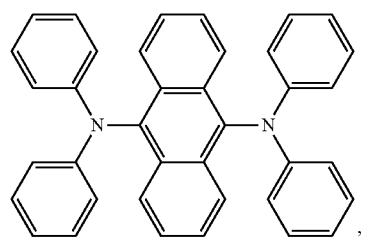
(F-6)
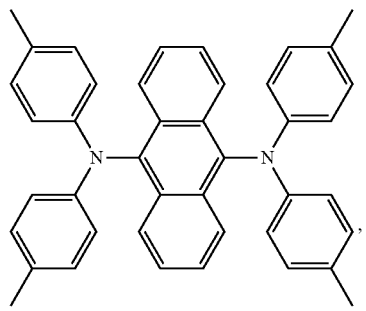
(F-7)
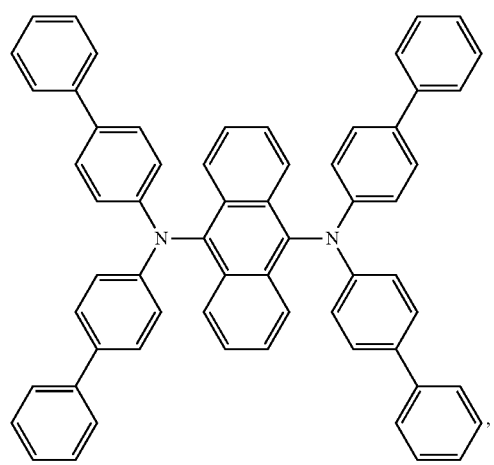
(F-8)
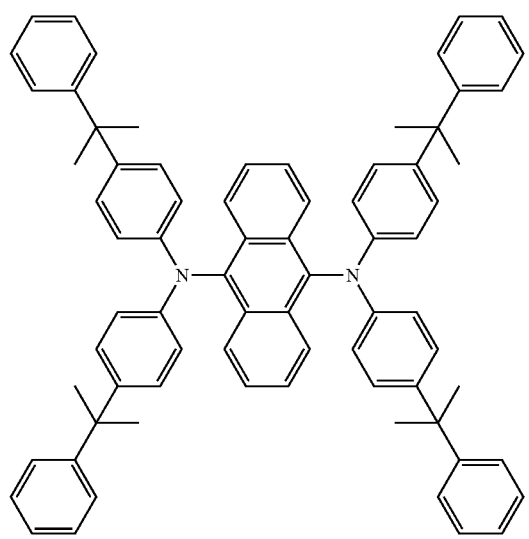
(F-9)
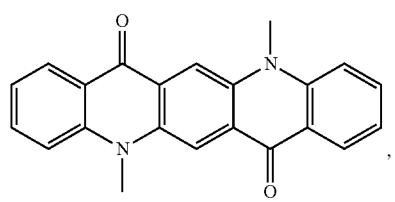
(F-10)
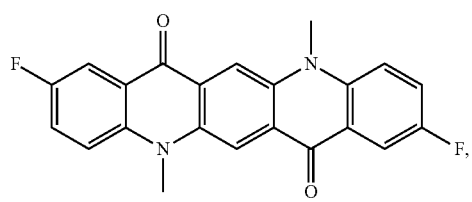
(F-11)
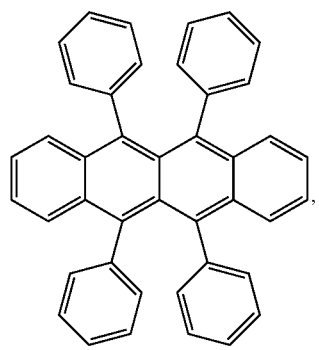
(F-12)
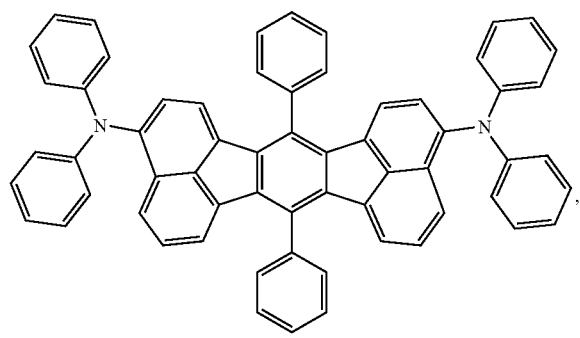

-continued
(F-13)
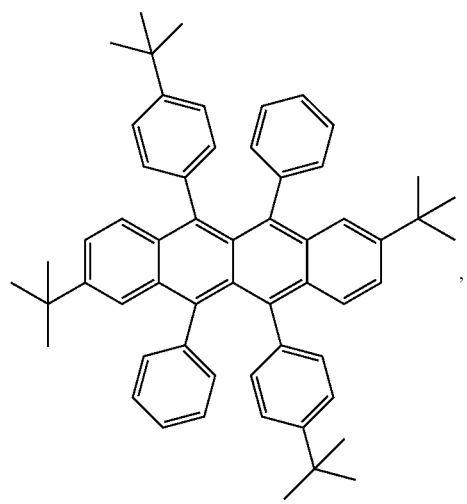
(F-14)
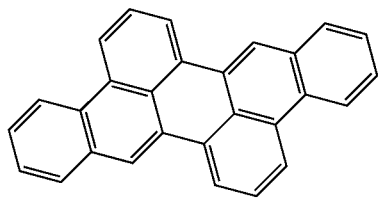
(F-15)
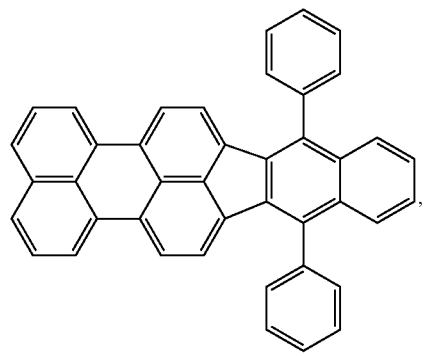
(F-16)
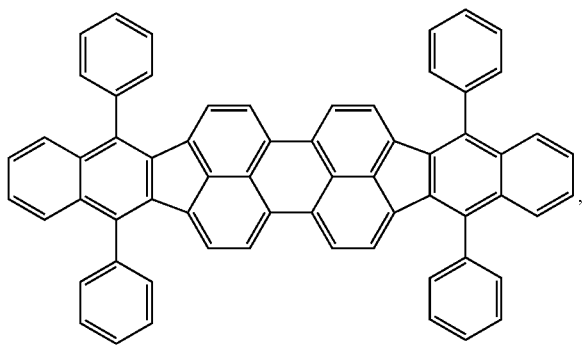
(F-17)
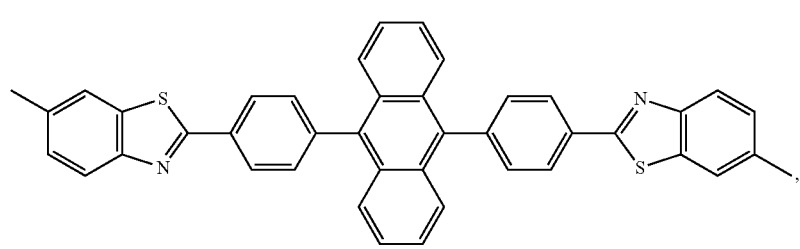
(F-18)
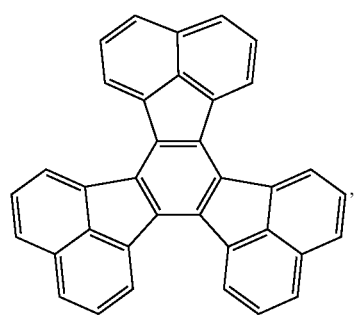
(F-19)
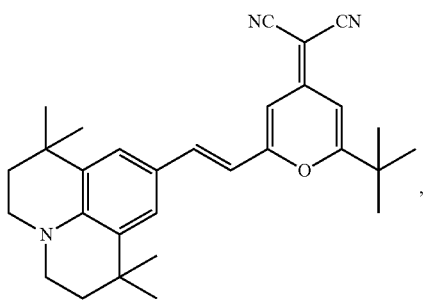

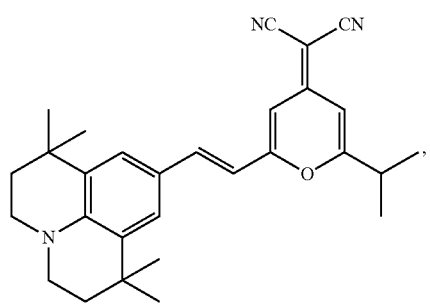 (F-20)

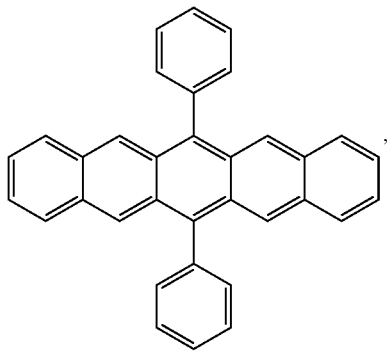 (F-21)

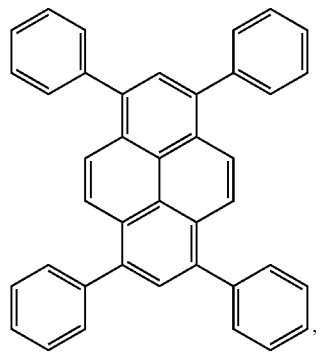 (F-22)

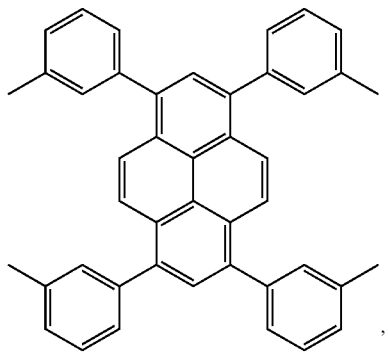 (F-23)

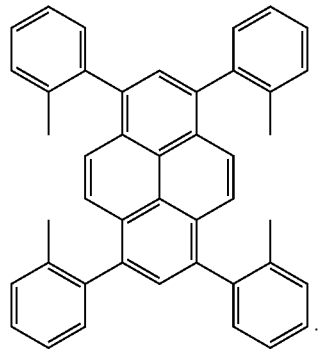 (F-24)

11. The organic electroluminescent device of claim 1, wherein a doping ratio of the exciplex is between 5 wt % and 80 wt %.

12. The organic electroluminescent device according to claim 10, wherein a doping ratio of the fluorescent doping dye is between 0.1 wt % and 10 wt %.

13. The organic electroluminescent device of claim 1, wherein in the exciplex, a mass ratio of the donor molecule to the acceptor molecule is between 1:5 and 5:1.

14. The organic electroluminescent device of claim 11, wherein the content of the exciplex is between 20 wt % and 50 wt % based on the total weight of the light-emitting layer.

15. The organic electroluminescent device of claim 12, wherein the content of the fluorescent doping dye is between 0.1 wt % and 3 wt % based on the total weight of the light-emitting layer.

16. The organic electroluminescent device of claim 1, wherein the organic electroluminescent device includes a first electrode, a second electrode, and an organic functional layer between the first electrode and the second electrode, the organic functional layer comprising a hole injection layer, a hole transport layer, the light-emitting layer, an electron transport layer, and an electron injection layer which are stacked.

17. The organic electroluminescent device of claim 16, wherein the wide band gap material is a compound as represented by a formula (W-1), the donor molecule is a compound as represented by a formula (D-1), and the acceptor molecule is a compound as represented by a formula (A-19):

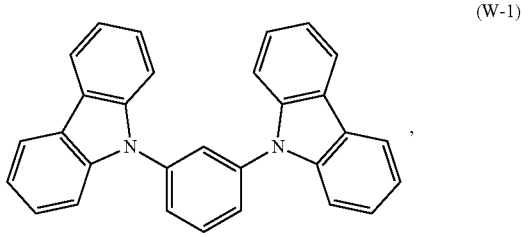 (W-1)

-continued

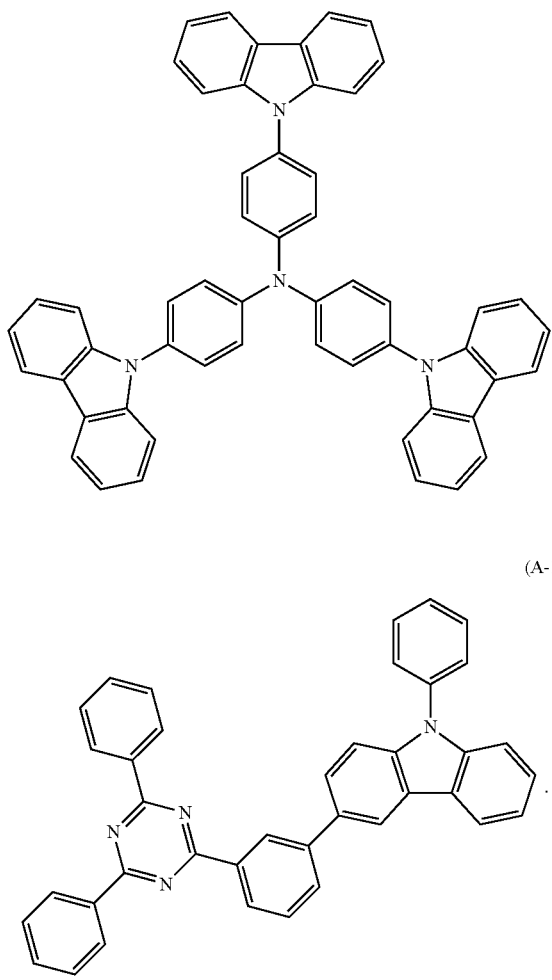

(D-1)

(A-19)

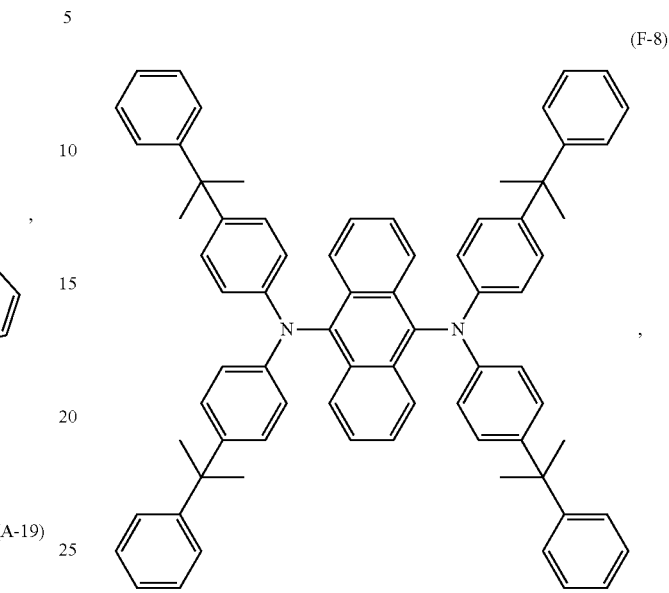

(F-8)

wherein the fluorescent doping dye has a content between 0.1 wt % and 3 wt %.

19. The organic electroluminescent device of claim 17, wherein a mass ratio of the donor molecule to the acceptor molecule is between 1:5 to 5:1, and wherein the exciplex has a content between 20 wt % and 50 wt %.

20. The organic electroluminescent device of claim 16, wherein the first electrode is made of ITO material, the hole injection layer is made of HATCN, the hole transport layer is made of TAPC, the electron transport layer is made of BPhen, the electron injection layer is made of electron injection material LiF, and the second electrode is made of Al.

* * * * *